United States Patent
Yonemura et al.

(10) Patent No.: US 10,292,395 B2
(45) Date of Patent: May 21, 2019

(54) 3H-PYRROLOPYRIDINE COMPOUND, N-OXIDE THEREOF OR SALT THEREOF, AGRICULTURAL AND HORTICULTURAL INSECTICIDE COMPRISING THE COMPOUND AND METHOD FOR USING THE SAME

(71) Applicant: Nihon Nohyaku Co., Ltd., Tokyo (JP)

(72) Inventors: Ikki Yonemura, Osaka (JP); Yusuke Sano, Osaka (JP); Akiyuki Suwa, Osaka (JP); Shunpei Fujie, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 15/775,296

(22) PCT Filed: Nov. 30, 2016

(86) PCT No.: PCT/JP2016/085483
§ 371 (c)(1),
(2) Date: May 10, 2018

(87) PCT Pub. No.: WO2017/094750
PCT Pub. Date: Jun. 8, 2017

(65) Prior Publication Data
US 2018/0352811 A1 Dec. 13, 2018

(30) Foreign Application Priority Data

Dec. 1, 2015 (JP) .................. 2015-234665
Sep. 5, 2016 (JP) .................. 2016-172747

(51) Int. Cl.
| C07D 401/04 | (2006.01) |
| A01N 43/90 | (2006.01) |
| A01N 43/40 | (2006.01) |
| A61K 31/437 | (2006.01) |
| A61K 31/4439 | (2006.01) |
| C07D 471/04 | (2006.01) |

(52) U.S. Cl.
CPC .......... *A01N 43/90* (2013.01); *A01N 43/40* (2013.01); *A61K 31/437* (2013.01); *A61K 31/4439* (2013.01); *C07D 401/04* (2013.01); *C07D 471/04* (2013.01)

(58) Field of Classification Search
CPC .... C07D 401/04; C07D 471/04; A01N 43/90; A01N 43/40
See application file for complete search history.

(56) References Cited

U.S. PATENT DOCUMENTS

| 2011/0039843 A1 | 2/2011 | Iwakoshi et al. |
| 2011/0124858 A1 | 5/2011 | Iwata et al. |
| 2012/0015975 A1 | 1/2012 | Takahashi et al. |
| 2012/0108586 A1 | 5/2012 | Iwakoshi et al. |
| 2012/0178779 A1 | 7/2012 | Takahashi et al. |
| 2012/0196891 A1 | 8/2012 | Iwakoshi |
| 2012/0245167 A1 | 9/2012 | Iwakoshi et al. |
| 2013/0190271 A1 | 7/2013 | Iwakoshi et al. |
| 2013/0252981 A1* | 9/2013 | Takahashi ............ C07D 403/04 514/269 |

(Continued)

FOREIGN PATENT DOCUMENTS

| JP | 2009-62355 A | 3/2009 |
| JP | 2009-280574 A | 12/2009 |

(Continued)

OTHER PUBLICATIONS

International Search Report for PCT/JP2016/085483 dated Jan. 24, 2017.

(Continued)

*Primary Examiner* — D Margaret M Seaman
(74) *Attorney, Agent, or Firm* — Knobbe Martens Olson & Bear LLP

(57) ABSTRACT

In crop production in the fields of agriculture, horticulture and the like, the damage caused by insect pests etc. is still immense, and insect pests resistant to existing insecticides have emerged. Under such circumstances, the development of novel agricultural and horticultural insecticides is desired. The present invention provides an agricultural and horticultural insecticide comprising, as an active ingredient, a 3H-pyrrolopyridine compound represented by the general formula (1):

[Chem. 1]

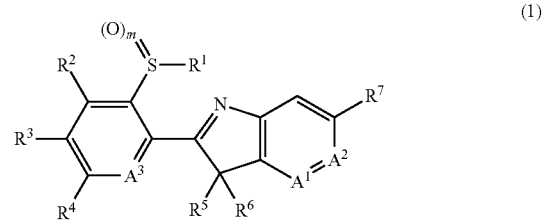

(wherein $A^1$, $A^2$, and $A^3$ each represent a nitrogen atom or a CH group, $R^1$ represents an ethyl group, $R^2$ and $R^4$ each represent a hydrogen atom, $R^3$ and $R^7$ each represent a haloalkyl group, $R^5$ and $R^6$ each represent a fluorine atom, and m represents 0 or 2), an N-oxide thereof or a salt thereof; and a method for using the agricultural and horticultural insecticide.

7 Claims, No Drawings

(56) References Cited

U.S. PATENT DOCUMENTS

| | | | |
|---|---|---|---|
| 2014/0194290 A1 | 7/2014 | Takahashi et al. | |
| 2015/0181880 A1 | 7/2015 | Takahashi et al. | |
| 2015/0197532 A1 | 7/2015 | Takahashi et al. | |
| 2016/0009715 A1 | 1/2016 | Takahashi et al. | |
| 2016/0159743 A1* | 6/2016 | Takahashi | A01N 43/76 546/261 |
| 2017/0250182 A1* | 8/2017 | Goel | H01L 29/267 |

FOREIGN PATENT DOCUMENTS

| | | |
|---|---|---|
| JP | 2010-275301 A | 12/2010 |
| JP | 2011-79774 A | 4/2011 |
| JP | 2012-131780 A | 7/2012 |
| JP | 2014-5263 A | 1/2014 |
| WO | WO 2012/086848 A1 | 6/2012 |
| WO | WO 2013/191113 A1 | 12/2013 |
| WO | WO 2014/148451 A1 | 9/2014 |
| WO | WO 2014/157600 A1 | 10/2014 |

OTHER PUBLICATIONS

International Preliminary Report on Patentability for PCT/JP2016/085483 dated Jul. 10, 2018.

* cited by examiner

3H-PYRROLOPYRIDINE COMPOUND, N-OXIDE THEREOF OR SALT THEREOF, AGRICULTURAL AND HORTICULTURAL INSECTICIDE COMPRISING THE COMPOUND AND METHOD FOR USING THE SAME

CROSS REFERENCE TO RELATED APPLICATIONS

This application is a U.S. National Phase Application of PCT International Application Number PCT/JP2016/085483, filed on Nov. 30, 2016, designating the United States of America and published in the Japanese language, which is an International Application of and claims the benefit of priority to Japanese Patent Application No. 2015-234665, filed on Dec. 1, 2015, and Japanese Patent Application No. 2016-172747, filed on Sep. 5, 2016. The disclosures of the above-referenced applications are hereby expressly incorporated by reference in their entireties.

TECHNICAL FIELD

The present invention relates to an agricultural and horticultural insecticide comprising a certain kind of 3H-pyrrolopyridine compound, an N-oxide thereof or a salt thereof as an active ingredient, and also relates to a method for using the agricultural and horticultural insecticide.

BACKGROUND ART

Various compounds have been examined for their potential as agricultural and horticultural insecticides, and among them, certain kinds of condensed heterocyclic compounds have been reported to be useful as insecticides (for example, see Patent Literature 1 to 8). None of these references disclose any condensed heterocyclic compound having a 3H-pyrrolopyridine ring.

CITATION LIST

Patent Literature

Patent Literature 1: JP-A 2009-280574
Patent Literature 2: JP-A 2010-275301
Patent Literature 3: JP-A 2011-79774
Patent Literature 4: JP-A 2012-131780
Patent Literature 5: WO 2012/086848
Patent Literature 6: WO 2013/018928
Patent literature 7: WO 2014/148451
Patent literature 8: WO 2014/157600

SUMMARY OF INVENTION

Technical Problem

In crop production in the fields of agriculture, horticulture and the like, the damage caused by insect pests etc. is still immense, and the emergence of insect pests resistant to existing insecticides is a growing problem. In addition, environmental protection on the earth is a global challenge to be addressed in every field, including the agricultural and horticultural field. Therefore, the development of novel compounds as agricultural and horticultural insecticides having low environmental burden is desired.

Solution to Problem

The present inventors conducted extensive research to solve the above-described problems. As a result, the present inventors found that a 3H-pyrrolopyridine compound represented by the general formula (1), an N-oxide thereof and a salt thereof are highly effective for the control of agricultural and horticultural pests and have low environmental burden. Based on this finding, the present inventors completed the present invention.

That is, the present invention relates to the following.

[1] A 3H-pyrrolopyridine compound represented by the general formula (1):

[Chem. 1]

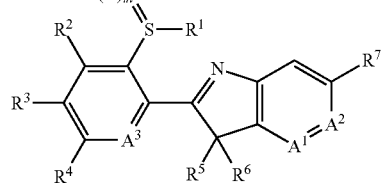

(1)

{wherein
$R^1$ represents
(a1) a ($C_1$-$C_6$) alkyl group;
(a2) a ($C_3$-$C_6$) cycloalkyl group;
(a3) a ($C_2$-$C_6$) alkenyl group; or
(a4) a ($C_2$-$C_6$) alkynyl group,
$R^2$ and $R^4$ may be the same or different and each represent
(b1) a hydrogen atom;
(b2) a halogen atom;
(b3) a hydroxyl group;
(b4) a formyl group;
(b5) a cyano group;
(b6) a ($C_1$-$C_6$) alkyl group;
(b7) a ($C_3$-$C_6$) cycloalkyl group;
(b8) a ($C_1$-$C_6$) alkoxy group;
(b9) a halo ($C_1$-$C_6$) alkyl group;
(b10) a halo ($C_3$-$C_6$) cycloalkyl group;
(b11) a halo ($C_1$-$C_6$) alkoxy group;
(b12) a ($C_1$-$C_6$) alkylthio group;
(b13) a ($C_1$-$C_6$) alkylsulfinyl group;
(b14) a ($C_1$-$C_6$) alkylsulfonyl group;
(b15) a halo ($C_1$-$C_6$) alkylthio group;
(b16) a halo ($C_1$-$C_6$) alkylsulfinyl group;
(b17) a halo ($C_1$-$C_6$) alkylsulfonyl group;
(b18) a ($C_3$-$C_6$) cycloalkyl ($C_1$-$C_6$) alkoxy group;
(b19) a $R^9(R^{10})N$ group (wherein $R^9$ and $R^{10}$ may be the same or different and each represent a hydrogen atom, a ($C_1$-$C_6$) alkyl group, a ($C_3$-$C_6$) cycloalkyl ($C_1$-$C_6$) alkyl group, a halo ($C_1$-$C_6$) alkyl group, a ($C_1$-$C_6$) alkylcarbonyl group, a ($C_1$-$C_6$) alkoxycarbonyl group or a phenylcarbonyl group);
(b20) a mono-($C_1$-$C_6$) alkylaminocarbonyl NH group;
(b21) a mono-($C_1$-$C_6$) alkylaminothiocarbonyl NH group;
(b22) a $C(R^9)=NOR^{10}$ group (wherein $R^9$ and $R^{10}$ are as defined above);
(b23) a carboxyl group;
(b24) a ($C_1$-$C_6$) alkoxycarbonyl group;
(b25) a $R^9(R^{10})N$ carbonyl group (wherein $R^9$ and $R^{10}$ are as defined above);
(b26) an aryl group;
(b27) an aryl group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo $(C_1-C_6)$ alkoxy group, a $(C_1-C_6)$ alkylthio group, a halo $(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group and a halo $(C_1-C_6)$ alkylsulfonyl group;
(b28) an aryl $(C_1-C_6)$ alkyl group;
(b29) an aryl $(C_1-C_6)$ alkyl group having, on the ring, 1 to 5 substituting groups which may be the same or different and are selected from the group consisting of a halogen atom, a $(C_1-C_6)$ alkyl group, a halo $(C_1-C_6)$ alkyl group, a $(C_1-C_6)$ alkoxy group, a halo $(C_1-C_6)$ alkoxy group, a $(C_1-C_6)$ alkylthio group, a halo $(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group and a halo $(C_1-C_6)$ alkylsulfonyl group;
(b30) an aryl $(C_1-C_6)$ alkyloxy group;
(b31) an aryl $(C_1-C_6)$ alkyloxy group having, on the ring, 1 to 5 substituting groups which may be the same or different and are selected from the group consisting of a halogen atom, a $(C_1-C_6)$ alkyl group, a halo $(C_1-C_6)$ alkyl group, a $(C_1-C_6)$ alkoxy group, a halo $(C_1-C_6)$ alkoxy group, a $(C_1-C_6)$ alkylthio group, a halo $(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group and a halo $(C_1-C_6)$ alkylsulfonyl group;
(b32) an aryl $(C_1-C_6)$ alkyl NH group;
(b33) an aryl $(C_1-C_6)$ alkyl NH group having, on the ring, 1 to 5 substituting groups which may be the same or different and are selected from the group consisting of a halogen atom, a $(C_1-C_6)$ alkyl group, a halo $(C_1-C_6)$ alkyl group, a $(C_1-C_6)$ alkoxy group, a halo $(C_1-C_6)$ alkoxy group, a $(C_1-C_6)$ alkylthio group, a halo $(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group and a halo $(C_1-C_6)$ alkylsulfonyl group;
(b34) a heterocyclic group; or
(b35) a heterocyclic group having, on the ring, 1 to 3 substituting groups which may be the same or different and are selected from the group consisting of a halogen atom, a $(C_1-C_6)$ alkyl group, a halo $(C_1-C_6)$ alkyl group, a $(C_1-C_6)$ alkoxy group, a halo $(C_1-C_6)$ alkoxy group, a $(C_1-C_6)$ alkylthio group, a halo $(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group and a halo $(C_1-C_6)$ alkylsulfonyl group, $R^3$ and $R^7$ may be the same or different and each represent
(c1) a hydrogen atom;
(c2) a halogen atom;
(c3) a hydroxyl group;
(c4) a formyl group;
(c5) a cyano group;
(c6) a $(C_1-C_6)$ alkyl group;
(c7) a $(C_3-C_6)$ cycloalkyl group;
(c8) a $(C_1-C_6)$ alkoxy group;
(c9) a halo $(C_1-C_6)$ alkyl group;
(c10) a halo $(C_3-C_6)$ cycloalkyl group;
(c11) a halo $(C_1-C_6)$ alkoxy group;
(c12) a $(C_1-C_6)$ alkylthio group;
(c13) a $(C_1-C_6)$ alkylsulfinyl group;
(c14) a $(C_1-C_6)$ alkylsulfonyl group;
(c15) a halo $(C_1-C_6)$ alkylthio group;
(c16) a halo $(C_1-C_6)$ alkylsulfinyl group;
(c17) a halo $(C_1-C_6)$ alkylsulfonyl group;
(c18) a $(C_3-C_6)$ cycloalkyl $(C_1-C_6)$ alkoxy group;
(c19) a $R^9(R^{10})N$ group (wherein $R^9$ and $R^{10}$ are as defined above);
(c20) a mono-$(C_1-C_6)$ alkylaminocarbonyl NH group;
(c21) a mono-$(C_1-C_6)$ alkylaminothiocarbonyl NH group;
(c22) a $C(R^9)=NOR^{10}$ group (wherein $R^9$ and $R^{10}$ are as defined above);
(c23) a carboxyl group;
(c24) a $(C_1-C_6)$ alkoxycarbonyl group;
(c25) a $R^9(R^{10})N$ carbonyl group (wherein $R^9$ and $R^{10}$ are as defined above);
(c26) an aryl group;
(c27) an aryl group having, on the ring, 1 to 5 substituting groups which may be the same or different and are selected from the group consisting of a halogen atom, a cyano group, a $(C_1-C_6)$ alkyl group, a halo $(C_1-C_6)$ alkyl group, a $(C_1-C_6)$ alkoxy group, a halo $(C_1-C_6)$ alkoxy group, a $(C_1-C_6)$ alkylthio group, a halo $(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group and a halo $(C_1-C_6)$ alkylsulfonyl group;
(c28) an aryl $(C_1-C_6)$ alkyl group;
(c29) an aryl $(C_1-C_6)$ alkyl group having, on the ring, 1 to 5 substituting groups which may be the same or different and are selected from the group consisting of a halogen atom, a $(C_1-C_6)$ alkyl group, a halo $(C_1-C_6)$ alkyl group, a $(C_1-C_6)$ alkoxy group, a halo $(C_1-C_6)$ alkoxy group, a $(C_1-C_6)$ alkylthio group, a halo $(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group and a halo $(C_1-C_6)$ alkylsulfonyl group;
(c30) an aryl $(C_1-C_6)$ alkyloxy group;
(c31) an aryl $(C_1-C_6)$ alkyloxy group having, on the ring, 1 to 5 substituting groups which may be the same or different and are selected from the group consisting of a halogen atom, a $(C_1-C_6)$ alkyl group, a halo $(C_1-C_6)$ alkyl group, a $(C_1-C_6)$ alkoxy group, a halo $(C_1-C_6)$ alkoxy group, a $(C_1-C_6)$ alkylthio group, a halo $(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group and a halo $(C_1-C_6)$ alkylsulfonyl group;
(c32) an aryl $(C_1-C_6)$ alkyl NH group;
(c33) an aryl $(C_1-C_6)$ alkyl NH group having, on the ring, 1 to 5 substituting groups which may be the same or different and are selected from the group consisting of a halogen atom, a $(C_1-C_6)$ alkyl group, a halo $(C_1-C_6)$ alkyl group, a $(C_1-C_6)$ alkoxy group, a halo $(C_1-C_6)$ alkoxy group, a $(C_1-C_6)$ alkylthio group, a halo $(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group and a halo $(C_1-C_6)$ alkylsulfonyl group;
(c34) a heterocyclic group; or
(c35) a heterocyclic group having, on the ring, 1 to 3 substituting groups which may be the same or different and are selected from the group consisting of a halogen atom, a $(C_1-C_6)$ alkyl group, a halo $(C_1-C_6)$ alkyl group, a $(C_1-C_6)$ alkoxy group, a halo $(C_1-C_6)$ alkoxy group, a $(C_1-C_6)$ alkylthio group, a halo $(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group and a halo $(C_1-C_6)$ alkylsulfonyl group, $R^5$ and $R^6$ may be the same or different and each represent
(d1) a halogen atom;
(d2) a cyano group;
(d3) a $(C_1-C_6)$ alkyl group;
(d4) a $(C_1-C_6)$ alkylthio group;
(d5) a $(C_1-C_6)$ alkylsulfonyl group; or
(d6) a $(C_1-C_6)$ alkoxycarbonyl group, or alternatively
(d7) $R^5$ and $R^6$ are joined together to form a 3- to 6-membered aliphatic ring, R³ and R⁴ may be combined to form an aromatic ring, A¹, A² and A³ may be the same or different and each represent a nitrogen atom, N—O or a C—R⁸ group (wherein R⁸ represents (e1) a hydrogen atom; or (e2) a halogen atom), and m represents 0, 1 or 2}, an N-oxide thereof or a salt thereof.

[2] The 3H-pyrrolopyridine compound according to the above [1], an N-oxide thereof or a salt thereof, wherein R¹ represents (a1) a ($C_1$-$C_6$) alkyl group, R² and R⁴ may be the same or different and each represent (b1) a hydrogen atom;
(b2) a halogen atom;
(b3) a hydroxyl group;
(b6) a ($C_1$-$C_6$) alkyl group;
(b7) a ($C_3$-$C_6$) cycloalkyl group;
(b8) a ($C_1$-$C_6$) alkoxy group;
(b9) a halo ($C_1$-$C_6$) alkyl group;
(b11) a halo ($C_1$-$C_6$) alkoxy group;
(b12) a ($C_1$-$C_6$) alkylthio group;
(b14) a ($C_1$-$C_6$) alkylsulfonyl group;
(b15) a halo ($C_1$-$C_6$) alkylthio group;
(b16) a halo ($C_1$-$C_6$) alkylsulfinyl group;
(b18) a ($C_3$-$C_6$) cycloalkyl ($C_1$-$C_6$) alkoxy group;
(b19) a R⁹(R¹⁰)N group (wherein R⁹ and R¹⁰ may be the same or different and each represent a hydrogen atom, a ($C_1$-$C_6$) alkyl group, a ($C_3$-$C_6$) cycloalkyl ($C_1$-$C_6$) alkyl group, a halo ($C_1$-$C_6$) alkyl group, a ($C_1$-$C_6$) alkylcarbonyl group, a ($C_1$-$C_6$) alkoxycarbonyl group or a phenylcarbonyl group);
(b20) a mono-($C_1$-$C_6$) alkylaminocarbonyl NH group;
(b21) a mono-($C_1$-$C_6$) alkylaminothiocarbonyl NH group;
(b22) a C(R⁹)=NOR¹⁰ group (wherein R⁹ and R¹⁰ are as defined above);
(b23) a carboxyl group;
(b24) a ($C_1$-$C_6$) alkoxycarbonyl group;
(b25) a R⁹(R¹⁰)N carbonyl group (wherein R⁹ and R¹⁰ are as defined above);
(b26) an aryl group;
(b27) an aryl group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(b28) an aryl ($C_1$-$C_6$) alkyl group;
(b29) an aryl ($C_1$-$C_6$) alkyl group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(b31) an aryl ($C_1$-$C_6$) alkyloxy group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(b33) an aryl ($C_1$-$C_6$) alkyl NH group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(b34) a heterocyclic group; or
(b35) a heterocyclic group having, on the ring, 1 to 3 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group, R³ and R⁷ may be the same or different and each represent (c1) a hydrogen atom;
(c2) a halogen atom;
(c6) a ($C_1$-$C_6$) alkyl group;
(c7) a ($C_3$-$C_6$) cycloalkyl group;
(c8) a ($C_1$-$C_6$) alkoxy group;
(c9) a halo ($C_1$-$C_6$) alkyl group;
(c11) a halo ($C_1$-$C_6$) alkoxy group;
(c12) a ($C_1$-$C_6$) alkylthio group;
(c14) a ($C_1$-$C_6$) alkylsulfonyl group;
(c15) a halo ($C_1$-$C_6$) alkylthio group;
(c16) a halo ($C_1$-$C_6$) alkylsulfinyl group;
(c18) a ($C_3$-$C_6$) cycloalkyl ($C_1$-$C_6$) alkoxy group;
(c19) a R⁹(R¹⁰)N group (wherein R⁹ and R¹⁰ may be the same or different and each represent a hydrogen atom, a ($C_1$-$C_6$) alkyl group, a ($C_3$-$C_6$) cycloalkyl ($C_1$-$C_6$) alkyl group, a halo ($C_1$-$C_6$) alkyl group, a ($C_1$-$C_6$) alkylcarbonyl group, a ($C_1$-$C_6$) alkoxycarbonyl group or a phenylcarbonyl group);
(c20) a mono-($C_1$-$C_6$) alkylaminocarbonyl NH group;
(c21) a mono-($C_1$-$C_6$) alkylaminothiocarbonyl NH group;
(c22) a C(R⁹)=NOR¹⁰ group (wherein R⁹ and R¹⁰ are as defined above);
(c23) a carboxyl group;
(c24) a ($C_1$-$C_6$) alkoxycarbonyl group;
(c25) a R⁹(R¹⁰)N carbonyl group (wherein R⁹ and R¹⁰ are as defined above);
(c26) an aryl group;
(c27) an aryl group having, on the ring, 1 to 5 substituting groups which may be the same or different and are selected from the group consisting of a halogen atom, a cyano group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(c28) an aryl ($C_1$-$C_6$) alkyl group;
(c29) an aryl ($C_1$-$C_6$) alkyl group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;

(c31) an aryl $(C_1$-$C_6)$ alkyloxy group having, on the ring, 1 to 5 substituting groups which may be the same or different and are selected from the group consisting of a halogen atom, a $(C_1$-$C_6)$ alkyl group, a halo $(C_1$-$C_6)$ alkyl group, a $(C_1$-$C_6)$ alkoxy group, a halo $(C_1$-$C_6)$ alkoxy group, a $(C_1$-$C_6)$ alkylthio group, a halo $(C_1$-$C_6)$ alkylthio group, a $(C_1$-$C_6)$ alkylsulfinyl group, a halo $(C_1$-$C_6)$ alkylsulfinyl group, a $(C_1$-$C_6)$ alkylsulfonyl group and a halo $(C_1$-$C_6)$ alkylsulfonyl group;

(c33) an aryl $(C_1$-$C_6)$ alkyl NH group having, on the ring, 1 to 5 substituting groups which may be the same or different and are selected from the group consisting of a halogen atom, a $(C_1$-$C_6)$ alkyl group, a halo $(C_1$-$C_6)$ alkyl group, a $(C_1$-$C_6)$ alkoxy group, a halo $(C_1$-$C_6)$ alkoxy group, a $(C_1$-$C_6)$ alkylthio group, a halo $(C_1$-$C_6)$ alkylthio group, a $(C_1$-$C_6)$ alkylsulfinyl group, a halo $(C_1$-$C_6)$ alkylsulfinyl group, a $(C_1$-$C_6)$ alkylsulfonyl group and a halo $(C_1$-$C_6)$ alkylsulfonyl group;

(c34) a heterocyclic group; or (c35) a heterocyclic group having, on the ring, 1 to 3 substituting groups which may be the same or different and are selected from the group consisting of a halogen atom, a $(C_1$-$C_6)$ alkyl group, a halo $(C_1$-$C_6)$ alkyl group, a $(C_1$-$C_6)$ alkoxy group, a halo $(C_1$-$C_6)$ alkoxy group, a $(C_1$-$C_6)$ alkylthio group, a halo $(C_1$-$C_6)$ alkylthio group, a $(C_1$-$C_6)$ alkylsulfinyl group, a halo $(C_1$-$C_6)$ alkylsulfinyl group, a $(C_1$-$C_6)$ alkylsulfonyl group and a halo $(C_1$-$C_6)$ alkylsulfonyl group, $R^5$ and $R^6$ may be the same or different and each represent (d1) a halogen atom;
(d2) a cyano group;
(d3) a $(C_1$-$C_6)$ alkyl group;
(d4) a $(C_1$-$C_6)$ alkylthio group;
(d5) a $(C_1$-$C_6)$ alkylsulfonyl group; or
(d6) a $(C_1$-$C_6)$ alkoxycarbonyl group, or alternatively
(d7) $R^5$ and $R^6$ are joined together to form a 3- to 6-membered aliphatic ring, $A^1$, $A^2$ and $A^3$ may be the same or different and each represent a nitrogen atom, N—O or a C—$R^8$ group (wherein $R^8$ represents (e1) a hydrogen atom), and m represents 0, 1 or 2.

[3] The 3H-pyrrolopyridine compound according to the above [1] or [2], an N-oxide thereof or a salt thereof, wherein $R^1$ represents (a1) a $(C_1$-$C_6)$ alkyl group, $R^2$ and $R^4$ may be the same or different and each represent
(b1) a hydrogen atom; or
(b34) a heterocyclic group, $R^3$ and $R^2$ may be the same or different and each represent
(c1) a hydrogen atom;
(c2) a halogen atom;
(c7) a $(C_3$-$C_6)$ cycloalkyl group;
(c9) a halo $(C_1$-$C_6)$ alkyl group;
(c22) a C($R^9$)=NO$R^{10}$ group (wherein $R^9$ and $R^{10}$ are as defined above);
(c27) an aryl group having, on the ring, 1 to 5 substituting groups which may be the same or different and are selected from the group consisting of a halogen atom, a cyano group, a $(C_1$-$C_6)$ alkyl group, a halo $(C_1$-$C_6)$ alkyl group, a $(C_1$-$C_6)$ alkoxy group, a halo $(C_1$-$C_6)$ alkoxy group, a $(C_1$-$C_6)$ alkylthio group, a halo $(C_1$-$C_6)$ alkylthio group, a $(C_1$-$C_6)$ alkylsulfinyl group, a halo $(C_1$-$C_6)$ alkylsulfinyl group, a $(C_1$-$C_6)$ alkylsulfonyl group and a halo $(C_1$-$C_6)$ alkylsulfonyl group;
(c28) an aryl $(C_1$-$C_6)$ alkyl group; or
(c34) a heterocyclic group, $R^5$ and $R^6$ may be the same or different and each represent
(d1) a halogen atom;
(d2) a cyano group;
(d3) a $(C_1$-$C_6)$ alkyl group; or
(d6) a $(C_1$-$C_6)$ alkoxycarbonyl group, $A^1$, $A^2$ and $A^3$ may be the same or different and each represent a nitrogen atom, N—O or a C—$R^8$ group (wherein $R^8$ represents (e1) a hydrogen atom), and m represents 1 or 2.

[4] Use of the 3H-pyrrolopyridine compound according to any of the above [1] to [3], an N-oxide thereof or a salt thereof as an active ingredient of an agricultural and horticultural insecticide.

[5] A method for using an agricultural and horticultural insecticide, the method comprising applying the active ingredient of the agricultural and horticultural insecticide specified in the above [4] to plants or soil.

[6] A method for controlling agricultural and horticultural pests, comprising applying the active ingredient of the agricultural and horticultural insecticide specified in the above [4] to plants or soil.

[7] An ectoparasite control agent comprising the 3H-pyrrolopyridine compound according to any of the above [1] to [3], an N-oxide thereof or a salt thereof as an active ingredient.

[8] A method for controlling ectoparasites, comprising applying an effective amount of the ectoparasite control agent according to the above [7] to ectoparasites.

Advantageous Effects of Invention

The 3H-pyrrolopyridine compound of the present invention, an N-oxide thereof and a salt thereof are not only highly effective as an agricultural and horticultural insecticide but also effective against pests which live on pets such as dogs and cats and domestic animals such as cattle and sheep.

DESCRIPTION OF EMBODIMENTS

In the definitions in connection with the general formula (1) representing the 3H-pyrrolopyridine compound of the present invention, an N-oxide thereof or a salt thereof, "halo" refers to a "halogen atom" and represents a chlorine atom, a bromine atom, an iodine atom or a fluorine atom.

The "$(C_1$-$C_6)$ alkyl group" refers to a straight-chain or branched-chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, a 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethyl propyl group, a 3,3-dimethylbutyl group or the like. The "$(C_2$-$C_6)$ alkenyl group" refers to a straight-chain or branched-chain alkenyl group of 2 to 6 carbon atoms, for example, a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, a 3,3-dimethyl-1-butenyl group or the like. The "$(C_2$-$C_6)$ alkynyl group" refers to a straight-chain or branched-chain alkynyl group of 2 to 6 carbon atoms, for example, an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, a 3,3-dimethyl-1-butynyl group or the like.

The "$(C_3-C_6)$ cycloalkyl group" refers to a cyclic alkyl group of 3 to 6 carbon atoms, for example, a cyclopropyl group, a cyclobutyl group, a cyclopentyl group, a cyclohexyl group or the like. The "$(C_1-C_6)$ alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, a 1-ethylpropyloxy group, a 1-methylbutyloxy group, a n-hexyloxy group, an isohexyloxy group, a 1,1,2-trimethylpropyloxy group or the like. The "$(C_2-C_6)$ alkenyloxy group" refers to a straight-chain or branched-chain alkenyloxy group of 2 to 6 carbon atoms, for example, a propenyloxy group, a butenyloxy group, a pentenyloxy group, a hexenyloxy group or the like. The "$(C_2-C_6)$ alkynyloxy group" refers to a straight-chain or branched-chain alkynyloxy group of 2 to 6 carbon atoms, for example, a propynyloxy group, a butynyloxy group, a pentynyloxy group, a hexynyloxy group or the like.

The "$(C_1-C_6)$ alkylthio group" refers to a straight-chain or branched-chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, a 1-ethylpropylthio group, a 1-methylbutylthio group, a n-hexylthio group, an isohexylthio group, a 1,1,2-trimethylpropylthio group or the like. The "$(C_1-C_6)$ alkylsulfinyl group" refers to a straight-chain or branched-chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, a 1-ethylpropylsulfinyl group, a 1-methylbutylsulfinyl group, a n-hexylsulfinyl group, an isohexylsulfinyl group, a 1,1,2-trimethylpropylsulfinyl group or the like. The "$(C_1-C_6)$ alkylsulfonyl group" refers to a straight-chain or branched-chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, a 1-ethylpropylsulfonyl group, a 1-methylbutylsulfonyl group, a n-hexylsulfonyl group, an isohexylsulfonyl group, a 1,1,2-trimethylpropylsulfonyl group or the like.

The "$(C_2-C_6)$ alkenylthio group" refers to a straight-chain or branched-chain alkenylthio group of 2 to 6 carbon atoms, for example, a propenylthio group, a butenylthio group, a pentenylthio group, a hexenylthio group or the like. The "$(C_2-C_6)$ alkynylthio group" refers to a straight-chain or branched-chain alkynylthio group of 2 to 6 carbon atoms, for example, a propynylthio group, a butynylthio group, a pentynylthio group, a hexynylthio group or the like.

The "$(C_2-C_6)$ alkenylsulfinyl group" refers to a straight-chain or branched-chain alkenylsulfinyl group of 2 to 6 carbon atoms, for example, a propenylsulfinyl group, a butenylsulfinyl group, a pentenylsulfinyl group, a hexenylsulfinyl group or the like. The "$(C_2-C_6)$ alkynylsulfinyl group" refers to a straight-chain or branched-chain alkynylsulfinyl group of 2 to 6 carbon atoms, for example, a propynylsulfinyl group, a butynylsulfinyl group, a pentynylsulfinyl group, a hexynylsulfinyl group or the like.

The "$(C_2-C_6)$ alkenylsulfonyl group" refers to a straight-chain or branched-chain alkenylsulfonyl group of 2 to 6 carbon atoms, for example, a propenylsulfonyl group, a butenylsulfonyl group, a pentenylsulfonyl group, a hexenylsulfonyl group or the like. The "$(C_2-C_6)$ alkynylsulfonyl group" refers to a straight-chain or branched-chain alkynylsulfonyl group of 2 to 6 carbon atoms, for example, a propynylsulfonyl group, a butynylsulfonyl group, a pentynylsulfonyl group, a hexynylsulfonyl group or the like.

The "$(C_3-C_6)$ cycloalkoxy group" refers to a cyclic alkoxy group of 3 to 6 carbon atoms, for example, a cyclopropoxy group, a cyclobutoxy group, a cyclopentyloxy group, a cyclohexyloxy group or the like. The "$(C_3-C_6)$ cycloalkylthio group" refers to a cyclic alkylthio group of 3 to 6 carbon atoms, for example, a cyclopropylthio group, a cyclobutylthio group, a cyclopentylthio group, a cyclohexylthio group or the like. The "$(C_3-C_6)$ cycloalkylsulfinyl group" refers to a cyclic alkylsulfinyl group of 3 to 6 carbon atoms, for example, a cyclopropylsulfinyl group, a cyclobutylsulfinyl group, a cyclopentylsulfinyl group, a cyclohexylsulfinyl group or the like. The "$(C_3-C_6)$ cycloalkylsulfonyl group" refers to a cyclic alkylsulfonyl group of 3 to 6 carbon atoms, for example, a cyclopropylsulfonyl group, a cyclobutylsulfonyl group, a cyclopentylsulfonyl group, a cyclohexylsulfonyl group or the like.

The above-mentioned "$(C_1-C_6)$ alkyl group",
"$(C_2-C_6)$ alkenyl group",
"$(C_2-C_6)$ alkynyl group",
"$(C_3-C_6)$ cycloalkyl group",
"$(C_3-C_6)$ cycloalkyloxy group",
"$(C_1-C_6)$ alkoxy group",
"$(C_2-C_6)$ alkenyloxy group",
"$(C_2-C_6)$ alkynyloxy group",
"$(C_1-C_6)$ alkylthio group",
"$(C_1-C_6)$ alkylsulfinyl group",
"$(C_1-C_6)$ alkylsulfonyl group",
"$(C_2-C_6)$ alkenylthio group",
"$(C_2-C_6)$ alkynylthio group",
"$(C_2-C_6)$ alkenylsulfinyl group",
"$(C_2-C_6)$ alkynylsulfinyl group",
"$(C_2-C_6)$ alkenylsulfonyl group",
"$(C_2-C_6)$ alkynylsulfonyl group",
"$(C_3-C_6)$ cycloalkylthio group",
"$(C_3-C_6)$ cycloalkylsulfinyl group" and
"$(C_3-C_6)$ cycloalkylsulfonyl group"
may be substituted with one or more halogen atoms at a substitutable position(s), and in the case where any of the above-listed groups is substituted with two or more halogen atoms, the halogen atoms may be the same or different.

The above-mentioned "groups substituted with one or more halogen atoms" are expressed as
a "halo $(C_1-C_6)$ alkyl group",
a "halo $(C_2-C_6)$ alkenyl group",
a "halo $(C_2-C_6)$ alkynyl group",
a "halo $(C_3-C_6)$ cycloalkyl group",
a "halo $(C_3-C_6)$ cycloalkyloxy group",
a "halo $(C_1-C_6)$ alkoxy group",
a "halo $(C_2-C_6)$ alkenyloxy group",
a "halo $(C_2-C_6)$ alkynyloxy group",
a "halo $(C_1-C_6)$ alkylthio group",
a "halo $(C_1-C_6)$ alkylsulfinyl group",
a "halo $(C_1-C_6)$ alkylsulfonyl group", a "halo ($C_2$-$C_6$) alkenylthio group",
a "halo ($C_2$-$C_6$) alkynylthio group",
a "halo ($C_2$-$C_6$) alkenylsulfinyl group",
a "halo ($C_2$-$C_6$) alkynylsulfinyl group",
a "halo ($C_2$-$C_6$) alkenylsulfonyl group",
a "halo ($C_2$-$C_6$) alkynylsulfonyl group",
a "halo ($C_3$-$C_6$) cycloalkylthio group",
a "halo ($C_3$-$C_6$) cycloalkylsulfinyl group" and
a "halo ($C_3$-$C_6$) cycloalkylsulfonyl group".

The expressions "($C_1$-$C_6$)", "($C_2$-$C_6$)", "($C_3$-$C_6$)", etc. each refer to the range of the number of carbon atoms in each group. The same definition holds true for groups in which two or more of the above-mentioned groups are coupled together, and for example, the "($C_1$-$C_6$) alkoxy ($C_1$-$C_6$) alkyl group" means that a straight-chain or branched-chain alkoxy group of 1 to 6 carbon atoms is bound to a straight-chain or branched-chain alkyl group of 1 to 6 carbon atoms.

The "3- to 6-membered aliphatic ring" which $R^5$ and $R^6$ bound to the same carbon atom are joined together to form is exemplified by a cyclopropyl group, a cyclobutyl group, a cyclopentyl group and a cyclohexyl group. The "aromatic ring or aromatic heterocyclic ring" which $R^3$ and $R^4$ are combined to form is exemplified by a quinolyl or naphthyl group having a phenyl ring formed of $R^3$ and $R^4$.

The "aryl group" refers to an aromatic hydrocarbon group of 6 to 10 carbon atoms, for example, a phenyl group, a 1-naphthyl group, a 2-naphthyl group or the like. Particularly preferred is a phenyl group.

The "heterocyclic group" and "heterocyclic ring" refer to a 5- or 6-membered monocyclic aromatic or 4- to 6-membered monocyclic non-aromatic heterocyclic group containing, as ring atoms, one or more carbon atoms and 1 to 4 heteroatoms selected from an oxygen atom, a sulfur atom and a nitrogen atom; and also refer to a condensed aromatic heterocyclic group formed by condensation of such a monocyclic aromatic heterocycle with a benzene ring or to a condensed non-aromatic heterocyclic group formed by condensation of such a monocyclic non-aromatic heterocycle with a benzene ring.

Examples of the "aromatic heterocyclic group" include monocyclic aromatic heterocyclic groups such as furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl, thiadiazolyl, triazolyl, tetrazolyl and triazinyl; and condensed aromatic heterocyclic groups such as quinolyl, isoquinolyl, quinazolyl, quinoxalyl, benzofuranyl, benzothienyl, benzoxazolyl, benzisoxazolyl, benzothiazolyl, benzimidazolyl, benzotriazolyl, indolyl, indazolyl, pyrrolopyrazinyl, imidazopyridinyl, imidazopyrazinyl, pyrazolopyridinyl, pyrazolothienyl and pyrazolotriazinyl.

Examples of the "non-aromatic heterocyclic group" include monocyclic non-aromatic heterocyclic groups such as oxetanyl, thietanyl, azetidinyl, pyrrolidinyl, pyrrolidinyl-2-one, piperidinyl, morpholinyl, thiomorpholinyl, piperazinyl, hexamethyleneiminyl, oxazolidinyl, thiazolidinyl, imidazolidinyl, oxazolinyl, thiazolinyl, isoxazolinyl, imidazolinyl, dioxolyl, dioxolanyl, dihydrooxadiazolyl, 2-oxo-pyrrolidin-1-yl, 2-oxo-1,3-oxazolidin-5-yl, 5-oxo-1,2,4-oxadiazolin-3-yl, 1,3-dioxolan-2-yl, 1,3-dioxan-2-yl, 1,3-dioxepan-2-yl, pyranyl, tetrahydropyranyl, thiopyranyl, tetrahydrothiopyranyl, 1-oxide tetrahydrothiopyranyl, 1,1-dioxide tetrahydrothiopyranyl, tetrahydrofuranyl, dioxanyl, pyrazolidinyl, pyrazolinyl, tetrahydropyrimidinyl, dihydrotriazolyl and tetrahydrotriazolyl.

Preferable examples of the "heterocyclic group" include isoxazolyl, pyrimidinyl, pyrazinyl, pyridyl, pyrazolyl, thiazolyl, thienyl, pyrrolyl, benzimidazolyl, benzofuranyl, benzothienyl, pyrrolidinyl-2-one.

Examples of the salts of the 3H-pyrrolopyridine compound represented by the general formula (1) of the present invention and an N-oxide thereof include inorganic acid salts such as hydrochlorides, sulfates, nitrates and phosphates; organic acid salts such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The 3H-pyrrolopyridine compound represented by the general formula (1) of the present invention, an N-oxide thereof and a salt thereof can have one or more chiral centers in the structural formula, and can exist as two or more kinds of optical isomers or diastereomers. All the optical isomers and mixtures of the isomers at any ratio are also included in the present invention. Further, the compound represented by the general formula (1) of the present invention, an N-oxide thereof and a salt thereof can exist as two kinds of geometric isomers due to a carbon-carbon double bond or a carbon-nitrogen double bond in the structural formula. All the geometric isomers and mixtures of the isomers at any ratio are also included in the present invention.

The 3H-pyrrolopyridine compound of the present invention, an oxide thereof or a salt thereof can be produced according to, for example, the production method described below, which is a non-limiting example in the present invention.

Production Method 1

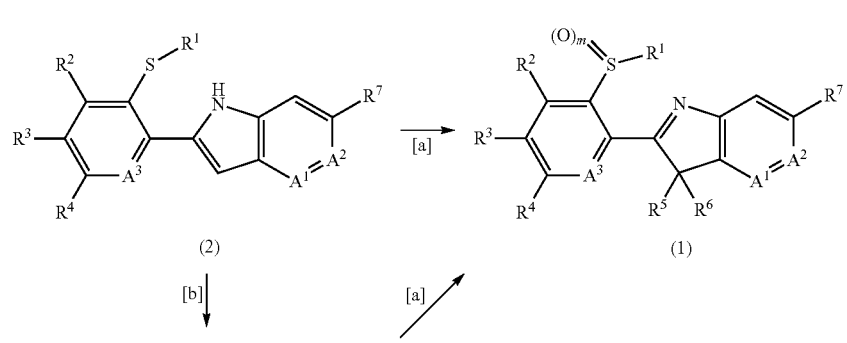

[Chem. 2]

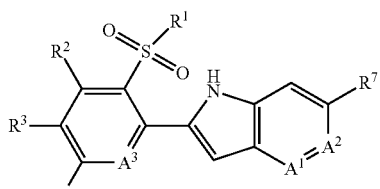

(1-1)

In the formula, $R^1$, $R^2$, $R^3$, $R^4$, $R^5$, $R^6$, $R^7$, $A^1$, $A^2$, $A^3$ and m are as defined above.

Production Method at [Step a]

The compound represented by the general formula (1) can be produced from 1H-pyrrolopyridine compound (2), which is produced by the method described in WO 2014/157600, according to the method described in the literature (Organic Letters, 13 (17), 4498-4501, 2011).

In this step, a fluorinating reagent is used for introduction of a fluorine atom as $R^5$ or $R^6$, and examples of the fluorinating reagent that can be used include N-fluoro-N'-(chloromethyl)triethylenediamine bis(tetrafluoroborate) (Selectfluor), $(PhSO_2)_2NF$ and N-fluoropyridinium triflate. Preferred is Selectfluor. The amount of the fluorinating reagent used is usually 1 to 10 molar equivalents relative to 1 mol of compound (2).

This step is usually performed in the presence of a base. Examples of the base that can be used include inorganic bases such as sodium hydroxide, potassium hydroxide, calcium hydroxide, barium hydroxide, sodium carbonate, potassium carbonate, potassium hydrogen carbonate, sodium hydrogen carbonate and cesium carbonate; and amines such as triethylamine, pyridine and piperidine. The amount of the base used is usually 1 to 10 molar equivalents relative to 1 mol of compound (2).

The organic solvent used in this reaction is not particularly limited and may be any solvent inert for the reaction. Examples of the organic solvent include nitrile solvents such as acetonitrile and benzonitrile; water; and a mixed solvent of two or more kinds of them.

The reaction temperature in this reaction is usually in the range of −20° C. to the boiling point of the solvent used. The reaction time is usually a few minutes to dozens of hours. After the reaction is completed, the compound of interest is isolated from the post-reaction mixture by a usual method. As needed, recrystallization, column chromatography, etc. can be employed for the purification of the compound of interest.

Production Method at [Step b]

The compound represented by the general formula (1-1) can be produced by oxidizing the 1H-pyrrolopyridine compound represented by the general formula (2) with an oxidizing agent in an inert solvent and performing the procedure described in the literature (Journal of Organic Chemistry, 18, 2784, 1964).

Examples of the oxidizing agent used for the oxidation in this reaction include peroxides such as a hydrogen peroxide solution, perbenzoic acid and m-chloroperoxybenzoic acid. The amount of the oxidizing agent used is appropriately selected from the range of a 2- to 5-fold molar amount relative to the 1H-pyrrolopyridine compound represented by the general formula (2).

The inert solvent used in this reaction may be any solvent that does not markedly inhibit the reaction, and the examples include aromatic hydrocarbons such as benzene, toluene and xylene; halogenated hydrocarbons such as methylene chloride and chloroform; halogenated aromatic hydrocarbons such as chlorobenzene and dichlorobenzene; nitriles such as acetonitrile; esters such as ethyl acetate; organic acids such as formic acid and acetic acid; and polar solvents such as water. One of these inert solvents may be used alone, or two or more of them may be used as a mixture.

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours. After the reaction is completed, the resulting oxide is isolated from the post-reaction mixture by a usual method. As needed, recrystallization, column chromatography, etc. can be employed for the purification of the compound of interest.

Alternatively, the resulting sulfonyl compound may be subjected to a reduction step without purification for conversion to a sulfinyl compound.

Examples of the reducing agent used in this reduction step include phosphorus trichloride. The amount of the reducing agent used is appropriately selected from the range of a 2- to 10-fold molar amount relative to the oxide.

The inert solvent used in this reaction may be any solvent that does not markedly inhibit the reaction, and the examples include aromatic hydrocarbons such as benzene, toluene and xylene; halogenated hydrocarbons such as methylene chloride and chloroform; halogenated aromatic hydrocarbons such as chlorobenzene and dichlorobenzene; nitriles such as acetonitrile; esters such as ethyl acetate; organic acids such as formic acid and acetic acid; and polar solvents such as water. One of these inert solvents may be used alone, or two or more of them may be used as a mixture.

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours. After the reaction is completed, the resulting 1H-pyrrolopyridine compound represented by the general formula (1-1) is isolated from the post-reaction mixture by a usual method. As needed, recrystallization, column chromatography, etc. can be employed for the purification of the compound of interest.

From the 1H-pyrrolopyridine compound represented by the general formula (1-1), the 3H-pyrrolopyridine compound represented by the general formula (1) can be produced by the same method as described in the above step [a].

The intermediate compound represented by the general formula (2-1) can be produced by the following method.

Production Method of Intermediate

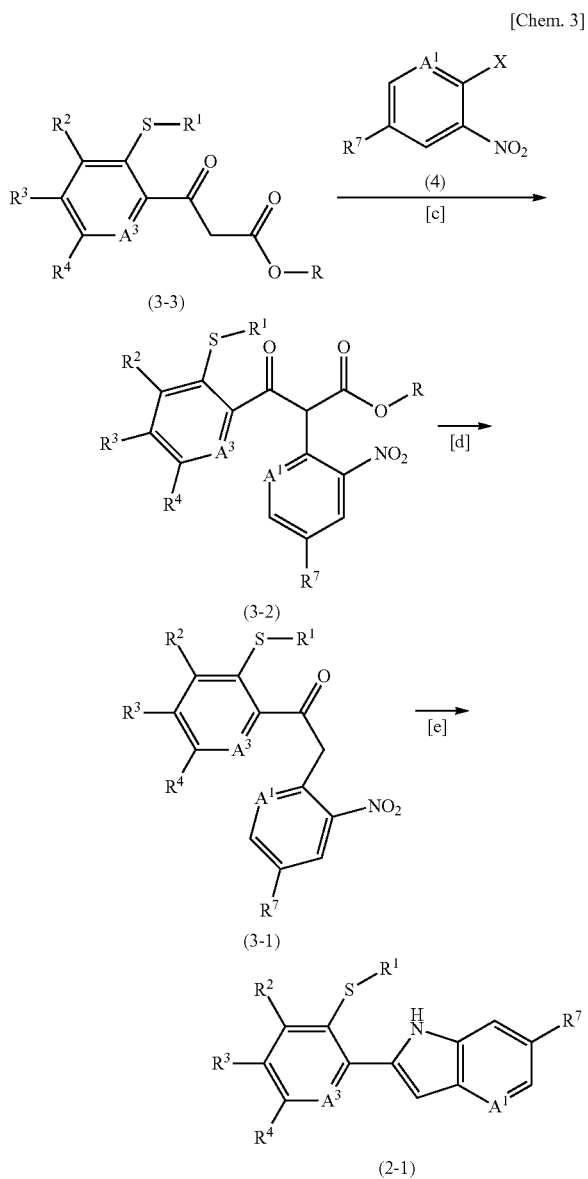

In the formula, $R^1$, $R^2$, $R^3$, $R^4$, $R^7$, $A^1$ and $A^3$ are as defined above, X represents a halogen atom, and R represents a tertiary alkyl group such as a t-butyl group and a 1-phenyl-2-methylpropan-2-yl group.

Production Method at [Step c]

The β-ketoester compound represented by the general formula (3-3) produced by Claisen condensation (Org. React. 1942, 1, 266) of an aromatic carboxylic acid ester and an acetic acid ester and/or ester exchange is reacted with the halogenated nitro compound represented by the general formula (4) in the presence of a base in an inert solvent to give the compound represented by the general formula (3-2).

The organic solvent used is not particularly limited and may be any solvent inert for the reaction. Examples of the organic solvent include ether solvents such as dioxane, 1,2-dimethoxyethane and tetrahydrofuran; aromatic hydrocarbon solvents such as toluene, benzene and xylene; amide solvents such as N,N-dimethylformamide, N,N-dimethylacetamide and N-methylpyrrolidone; and a mixed solvent of two or more kinds of them.

Examples of the base that can be used include inorganic bases such as sodium hydroxide, potassium hydroxide, calcium hydroxide, barium hydroxide, sodium carbonate, potassium carbonate, potassium hydrogen carbonate, sodium hydrogen carbonate, cesium carbonate and potassium phosphate; alkoxides such as potassium t-butoxide, sodium methoxide and sodium ethoxide; alkali metal hydrides such as sodium hydride and potassium hydride; and amines such as triethylamine, pyridine and piperidine. The amount of the base used is usually 1 to 10 molar equivalents relative to 1 mol of compound (3-3).

Since this reaction is an equimolar reaction of compound (3-3) and compound (4), they are basically used in equimolar amounts, but either of them may be used in an excess amount.

The reaction temperature is usually in the range of room temperature to the boiling point of the solvent used. The reaction time is usually a few minutes to dozens of hours. The reaction is preferably performed under the atmosphere of an inert gas. After the reaction is completed, the compound of interest is isolated from the post-reaction mixture by a usual method. As needed, recrystallization, column chromatography, etc. can be employed for the purification of the compound of interest.

Production Method at [Step d]

The compound represented by the general formula (3-2) is treated with an acid in the presence or absence of a solvent to give the compound represented by the general formula (3-1).

Examples of the acid used in this reaction include inorganic acids such as hydrochloric acid, sulfuric acid and nitric acid; organic acids such as formic acid, acetic acid, propionic acid, trifluoroacetic acid and benzoic acid; and sulfonic acids such as methanesulfonic acid and trifluoromethanesulfonic acid. The amount of the acid used is appropriately selected from the range of a 1- to 10-fold molar amount relative to the ester compound represented by the general formula (3-2). In some cases, the acid can be used as the solvent as well.

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; amides such as dimethylformamide and dimethylacetamide; ketones such as acetone and methyl ethyl ketone; and polar solvents such as 1,3-dimethyl-2-imidazolidinone. One of these inert solvents may be used alone, or two or more of them may be used as a mixture. In the case where the acid is used as the solvent, it is not necessary to use another solvent.

The reaction temperature is in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by a usual method. As needed, recrystallization, column chromatography, etc. can be employed for the purification of the compound of interest.

Production Method at [Step e]

The reaction in this step is reduction and dehydration of the nitro compound represented by the general formula (3-1) to produce the 1H-pyrrolopyridine compound represented by the general formula (2-1).

For the above reduction, the conditions for reduction of nitro groups described in the known literature (see "New Lecture of Experimental Chemistry (Shin Jikken Kagaku Kouza)", vol. 15, Oxidation and Reduction II, 1977, edited by the Chemical Society of Japan, published by Maruzen) can be used.

Examples of the inert solvent that can be used in this reaction include alcohols such as methanol and ethanol; ethers such as tetrahydrofuran and dioxane; organic acids such as formic acid and acetic acid; and water. One of these inert solvents may be used alone, or two or more of them may be used as a mixture. An aqueous solution of an acid used as the reducing agent in this reaction can be used as the inert solvent as well.

Examples of the reducing agent that can be used in this reaction include metal-acid and metal-salt. Examples of the metal include iron, tin and zinc, examples of the acid include inorganic acids such as hydrochloric acid and sulfuric acid and organic acids such as acetic acid, and examples of the salt include tin chloride and ammonium chloride. These metals may be used in combination, these acids may be used in combination, and these salts may be used in combination. As for the amount of the reducing agent used, the amount of the metal is appropriately selected from the range of an about 1- to 10-fold molar amount relative to the nitro compound represented by the general formula (3-1), and the amount of the acid or the salt is appropriately selected from the range of an about 0.05- to 10-fold molar amount relative to the nitro compound represented by the general formula (3-1). The reaction temperature can be selected from the range of about 0 to 150° C. The reaction time varies with the reaction scale, the reaction temperature and the like, but is basically selected as appropriate from the range of a few minutes to about 48 hours. The reduction in this step can also be performed by catalytic hydrogenation in the presence of a catalyst. Examples of the catalyst include palladium carbon. After the reaction is completed, the compound of interest is isolated from the post-reaction mixture by a usual method. As needed, recrystallization, distillation, column chromatography, etc. can be employed for the purification of the compound of interest. The 1H-pyrrolopyridine compound represented by the general formula (2-1) produced according to the production scheme described above is subjected to the reactions in Production Method 1 to give the 3H-pyrrolopyridine compound represented by the general formula (1).

The intermediate compound can also be produced according to the production method described in WO 2014/157600.

Specific examples of the compound of the present invention are shown below. In the following tables, Me stands for a methyl group, Et stands for an ethyl group, n-Pr stands for a n-propyl group, i-Pr stands for an isopropyl group, c-Pr stands for a cyclopropyl group, t-Bu stands for a tert-butyl group, c-Pent stands for a cyclopentyl group, Ph stands for a phenyl group, Bn stands for a benzyl group, Py stands for a pyridyl group; Pyrazol stands for a pyrazolyl group, Pyrol stands for a pyrrolyl group, Triazol stands for a triazolyl group, Pyrimidin stands for a pyrimidyl group, Thiazol stands for a thiazolyl group, Pyrrolid stands for a pyrrolidinyl group, Isoxazol stands for an isoxazolyl group, Isoxazolin stands for an isoxazolinyl group, Thiophen stands for a thienyl group, Benzofuran stands for a benzofuranyl group, and Benzothiophen stands for a benzothienyl group.

Shown in the column of "Physical property" is a melting point (° C.) or "NMR". NMR data are shown in Table 4.

[Chem. 4]

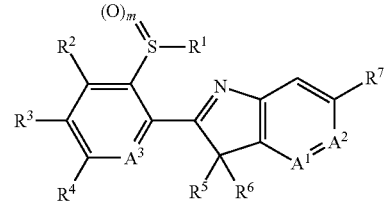

(1)

TABLE 1

| Compound No. | $A^1$ | $A^3$ | $R^3$ | $R^5$ | $R^6$ | $R^7$ | m | Physical property |
|---|---|---|---|---|---|---|---|---|
| 1-1 | N | CH | $CF_3$ | F | F | $CF_3$ | 2 | 120-122 |
| 1-2 | N | CH | $CF_3$ | F | $CO_2Et$ | $CF_3$ | 1 | 142-144 |
| 1-3 | N | CH | $CF_3$ | F | $CO_2Et$ | $CF_3$ | 2 | 165-167 |
| 1-4 | N | CH | $CF_3$ | F | F | $CF_2CF_3$ | 2 | NMR |
| 1-5 | N | CH | $CF_3$ | F | CN | $CF_3$ | 2 | NMR |
| 1-6 | N | CH | $CF_3$ | F | $CO_2Me$ | $CF_3$ | 2 | NMR |
| 1-7 | N | CH | $CF_3$ | F | $CO_2Me$ | $CF_3$ | 1 | NMR |
| 1-8 | N | CH | $CF_3$ | F | $CO_2Me$ | $CF_3$ | 1 | NMR |
| 1-9 | N | N | $CF_3$ | F | F | $CF_3$ | 1 | NMR |
| 1-10 | N | N | $CF_3$ | F | F | $CF_3$ | 2 | NMR |
| 1-11 | N | N | I | F | F | $CF_3$ | 2 | 156-158 |
| 1-12 | N | N | I | F | F | $CF_3$ | 1 | 170-172 |
| 1-13 | $N^+$—$O^-$ | N | I | F | F | $CF_3$ | 1 | 160-161 |
| 1-14 | N | N | c-Pr | F | F | $CF_3$ | 0 | 165-166 |
| 1-15 | N | N | c-Pr | F | F | $CF_3$ | 1 | 150-151 |
| 1-16 | N | N | c-Pr | F | F | $CF_3$ | 2 | 120-121 |
| 1-17 | N | N | Ph | F | F | $CF_3$ | 2 | |
| 1-18 | N | N | 3-F—Ph | F | F | $CF_3$ | 2 | 186-187 |
| 1-19 | N | N | 4-F—Ph | F | F | $CF_3$ | 2 | 179-180 |
| 1-20 | N | N | 3-$CF_3$—Ph | F | F | $CF_3$ | 2 | 137-138 |
| 1-21 | N | N | 4-$CF_3$—Ph | F | F | $CF_3$ | 2 | 163-164 |

TABLE 1-continued $A^2$ represents CH, $R^1$ represents an ethyl group, and $R^2$ and $R^4$ each represent a hydrogen atom.

| Compound No. | $R^3$ | $R^5$ | $R^6$ | $R^7$ | m | Physical property |
|---|---|---|---|---|---|---|
| 1-22 | 1-Me-Pyrazol-3-yl | F | F | $CF_3$ | 2 | |
| 1-23 | 1-$CHF_2$-Pyrazol-3-yl | F | F | $CF_3$ | 2 | |
| 1-24 | 1-Me-5-OMe-Pyrazol-3-yl | F | F | $CF_3$ | 2 | |
| 1-25 | 1-Me-5-$OCHF_2$-Pyrazol-3-yl | F | F | $CF_3$ | 2 | |
| 1-26 | 3-$OCHF_2$-Pyrazol-1-yl | F | F | $CF_3$ | 2 | |
| 1-27 | 3-Br-Pyrol-1-yl | F | F | $CF_3$ | 2 | |
| 1-28 | 1,2,4-Triazol-1-yl | F | F | $CF_3$ | 2 | |
| 1-29 | 3-Me-1,2,4-Triazol-1-yl | F | F | $CF_3$ | 2 | |
| 1-30 | 3-$CF_3$-1,2,4-Triazol-1-yl | F | F | $CF_3$ | 2 | |
| 1-31 | CH=NOH | F | F | $CF_3$ | 2 | |
| 1-32 | CH=NOEt | F | F | $CF_3$ | 2 | |
| 1-33 | CH=$NOCH_2CHF_2$ | F | F | $CF_3$ | 2 | |
| 1-34 | CH=$NOCH_2CF_3$ | F | F | $CF_3$ | 2 | 136-137 |
| 1-35 | CH=$NOCH_2$—c-Pr | F | F | $CF_3$ | 2 | |
| 1-36 | C(Me)=NOEt | F | F | $CF_3$ | 2 | |
| 1-37 | C(Me)=$NOCH_2CHF_2$ | F | F | $CF_3$ | 2 | |
| 1-38 | C(Me)=$NOCH_2CF_3$ | F | F | $CF_3$ | 2 | |
| 1-39 | C(Me)=$NOCH_2$—c-Pr | F | F | $CF_3$ | 2 | |
| 1-40 | C($CF_3$)=NOEt | F | F | $CF_3$ | 2 | |
| 1-41 | C($CF_3$)=$NOCH_2CHF_2$ | F | F | $CF_3$ | 2 | |
| 1-42 | C($CF_3$)=$NOCH_2$—c-Pr | F | F | $CF_3$ | 2 | |
| 1-43 | 5-$CF_3$—Py-2-yl | F | F | $CF_3$ | 2 | |
| 1-44 | Pyrimidin-2-yl | F | F | $CF_3$ | 2 | |
| 1-45 | $CO_2H$ | F | F | $CF_3$ | 2 | |
| 1-46 | $CO_2Et$ | F | F | $CF_3$ | 2 | |
| 1-47 | $CO_2$—i-Pr | F | F | $CF_3$ | 2 | |
| 1-48 | $CO_2$—t-Bu | F | F | $CF_3$ | 2 | |
| 1-49 | CONH—i-Pr | F | F | $CF_3$ | 2 | |
| 1-50 | CONH—$CH_2CF_3$ | F | F | $CF_3$ | 2 | |
| 1-51 | CON(Me)Et | F | F | $CF_3$ | 2 | |
| 1-52 | $NH_2$ | F | F | $CF_3$ | 2 | |
| 1-53 | NHCOMe | F | F | $CF_3$ | 2 | |
| 1-54 | NHCO—i-Pr | F | F | $CF_3$ | 2 | |
| 1-55 | NHCOPh | F | F | $CF_3$ | 2 | |
| 1-56 | $NHCO_2Me$ | F | F | $CF_3$ | 2 | |
| 1-57 | $NHCO_2$—i-Pr | F | F | $CF_3$ | 2 | |
| 1-58 | $NHCO_2$—t-Bu | F | F | $CF_3$ | 2 | |
| 1-59 | NHCONHMe | F | F | $CF_3$ | 2 | |
| 1-60 | NHCONH—i-Pr | F | F | $CF_3$ | 2 | |
| 1-61 | NHCONH—t-Bu | F | F | $CF_3$ | 2 | |
| 1-62 | i-Pr | F | F | $CF_3$ | 2 | |
| 1-63 | SMe | F | F | $CF_3$ | 2 | |
| 1-64 | $SO_2Me$ | F | F | $CF_3$ | 2 | |
| 1-65 | SEt | F | F | $CF_3$ | 2 | |
| 1-66 | $SO_2Et$ | F | F | $CF_3$ | 2 | |
| 1-67 | $SCF_3$ | F | F | $CF_3$ | 2 | |
| 1-68 | $SOCF_3$ | F | F | $CF_3$ | 2 | |
| 1-69 | $OCHF_2$ | F | F | $CF_3$ | 2 | |
| 1-70 | OH | F | F | $CF_3$ | 2 | |
| 1-71 | OEt | F | F | $CF_3$ | 2 | 165-167 |
| 1-72 | $OCH_2$—c-Pr | F | F | $CF_3$ | 2 | |
| 1-73 | NHCSNH—i-Pr | F | F | $CF_3$ | 2 | |
| 1-74 | NHCSNH—i-Pr | F | F | $CF_3$ | 2 | |
| 1-75 | 5-Me-Thiazol-2-yl | F | F | $CF_3$ | 2 | |
| 1-76 | 5-Me-Isoxazol-3-yl | F | F | $CF_3$ | 2 | |
| 1-77 | Bn | F | F | $CF_3$ | 2 | |
| 1-78 | 4-F-Bn | F | F | $CF_3$ | 2 | |
| 1-79 | 4-$CF_3$-Bn | F | F | $CF_3$ | 2 | |
| 1-80 | 4-F-BnO | F | F | $CF_3$ | 2 | |
| 1-81 | 4-$CF_3$-BnO | F | F | $CF_3$ | 2 | 199-201 |
| 1-82 | 4-F-BnNH | F | F | $CF_3$ | 2 | |
| 1-83 | 4-$CF_3$-BnNH | F | F | $CF_3$ | 2 | |
| 1-84 | Pyrrolid-2-one-1-yl | F | F | $CF_3$ | 2 | |
| 1-85 | 5,5-$Me_2$-Isoxazolin-3-yl | F | F | $CF_3$ | 2 | |

$A^1$ and $A^3$ each represent a nitrogen atom, $A^2$ represents CH, $R^1$ represents an ethyl group, and $R^2$ and $R^4$ each represents a hydrogen atom.

| Compound No. | $R^3$ | $R^4$ | $R^5$ | $R^6$ | $R^7$ | m | Physical property |
|---|---|---|---|---|---|---|---|
| 1-86 | $CF_3$ | H | Me | Me | $CF_3$ | 2 | |
| 1-87 | $CF_3$ | H | F | F | $OCH_2CF_3$ | 2 | |
| 1-88 | $CF_3$ | H | F | F | $SCF_3$ | 2 | |
| 1-89 | $CF_3$ | H | F | F | $N(Me)CH_2CF_3$ | 2 | |
| 1-90 | $CF_3$ | H | F | F | Br | 2 | |
| 1-91 | $CF_3$ | H | | c-Pr | $CF_3$ | 2 | |
| 1-92 | $CF_3$ | H | | c-Pent | $CF_3$ | 2 | |

TABLE 1-continued

| | | | | | | | |
|---|---|---|---|---|---|---|---|
| 1-93 | CF$_3$ | H | SMe | SMe | CF$_3$ | 2 | |
| 1-94 | CF$_3$ | H | F | SO$_2$Me | CF$_3$ | 2 | |
| 1-95 | H | CF$_3$ | F | F | CF$_3$ | 2 | |
| 1-96 | H | I | F | F | CF$_3$ | 2 | |
| 1-97 | H | c-Pr | F | F | CF$_3$ | 2 | |
| 1-98 | H | Ph | F | F | CF$_3$ | 2 | |
| 1-99 | H | 3-F—Ph | F | F | CF$_3$ | 2 | 189-190 |
| 1-100 | H | 4-F—Ph | F | F | CF$_3$ | 2 | 217-218 |
| 1-101 | H | 3-CF$_3$—Ph | F | F | CF$_3$ | 2 | |
| 1-102 | H | 4-CF$_3$—Ph | F | F | CF$_3$ | 2 | |
| 1-103 | H | 1-Me-Pyrazol-3-yl | F | F | CF$_3$ | 2 | |
| 1-104 | H | 1-CHF$_2$-Pyrazol-3-yl | F | F | CF$_3$ | 2 | |
| 1-105 | H | 1-Me-5-OMe-Pyrazol-3-yl | F | F | CF$_3$ | 2 | |
| 1-106 | H | 1-Me-5-OCHF$_2$-Pyrazol-3-yl | F | F | CF$_3$ | 2 | |
| 1-107 | H | 3-OCHF$_2$-Pyrazol-1-yl | F | F | CF$_3$ | 2 | |
| 1-108 | H | 3-Br-Pyrol-1-yl | F | F | CF$_3$ | 2 | |
| 1-109 | H | 1,2,4-Triazol-1-yl | F | F | CF$_3$ | 2 | 223-224 |
| 1-110 | H | 3-Me-1,2,4-Triazol-1-yl | F | F | CF$_3$ | 2 | |
| 1-111 | H | 3-CF$_3$-1,2,4-Triazol-1-yl | F | F | CF$_3$ | 2 | |
| 1-112 | H | CH=NOH | F | F | CF$_3$ | 2 | |
| 1-113 | H | CH=NOEt | F | F | CF$_3$ | 2 | |
| 1-114 | H | CH=NOCH$_2$CHF$_2$ | F | F | CF$_3$ | 2 | |
| 1-115 | H | CH=NOCH$_2$CF$_3$ | F | F | CF$_3$ | 2 | |
| 1-116 | H | CH=NOCH$_2$—c-Pr | F | F | CF$_3$ | 2 | |
| 1-117 | H | C(Me)=NOEt | F | F | CF$_3$ | 2 | |
| 1-118 | H | C(Me)=NOCH$_2$CHF$_2$ | F | F | CF$_3$ | 2 | |
| 1-119 | H | C(Me)=NOCH$_2$CF$_3$ | F | F | CF$_3$ | 2 | |
| 1-120 | H | C(Me)=NOCH$_2$—c-Pr | F | F | CF$_3$ | 2 | |
| 1-121 | H | C(CF$_3$)=NOEt | F | F | CF$_3$ | 2 | |
| 1-122 | H | C(CF$_3$)=NOCH$_2$CHF$_2$ | F | F | CF$_3$ | 2 | |
| 1-123 | H | C(CF$_3$)=NOCH$_2$—c-Pr | F | F | CF$_3$ | 2 | |
| 1-124 | H | 5-CF$_3$=Py-2-yl | F | F | CF$_3$ | 2 | |
| 1-125 | H | Pyrimidin-2-yl | F | F | CF$_3$ | 2 | |
| 1-126 | H | CO$_2$H | F | F | CF$_3$ | 2 | |
| 1-127 | H | CO$_2$Et | F | F | CF$_3$ | 2 | |
| 1-128 | H | CO$_2$—i-Pr | F | F | CF$_3$ | 2 | |
| 1-129 | H | CO$_2$—t-Bu | F | F | CF$_3$ | 2 | |
| 1-130 | H | CONH—i-Pr | F | F | CF$_3$ | 2 | |
| 1-131 | H | CONH—CH$_2$CF$_3$ | F | F | CF$_3$ | 2 | |
| 1-132 | H | CON(Me)Et | F | F | CF$_3$ | 2 | |
| 1-133 | H | NH$_2$ | F | F | CF$_3$ | 2 | |
| 1-134 | H | NHCOMe | F | F | CF$_3$ | 2 | |
| 1-135 | H | NHCO—i-Pr | F | F | CF$_3$ | 2 | |
| 1-136 | H | NHCOPh | F | F | CF$_3$ | 2 | |
| 1-137 | H | NHCO$_2$Me | F | F | CF$_3$ | 2 | |
| 1-138 | H | NHCO$_2$—i-Pr | F | F | CF$_3$ | 2 | |
| 1-139 | H | NHCO$_2$—t-Bu | F | F | CF$_3$ | 2 | |
| 1-140 | H | NHCONHMe | F | F | CF$_3$ | 2 | |
| 1-141 | H | NHCONH—i-Pr | F | F | CF$_3$ | 2 | |
| 1-142 | H | NHCONH—t-Bu | F | F | CF$_3$ | 2 | |
| 1-143 | H | i-Pr | F | F | CF$_3$ | 2 | |
| 1-144 | H | SMe | F | F | CF$_3$ | 2 | |
| 1-145 | H | SO$_2$Me | F | F | CF$_3$ | 2 | |
| 1-146 | H | SEt | F | F | CF$_3$ | 2 | |
| 1-147 | H | SO$_2$Et | F | F | CF$_3$ | 2 | |
| 1-148 | H | SCF$_3$ | F | F | CF$_3$ | 2 | |
| 1-149 | H | SOCF$_3$ | F | F | CF$_3$ | 2 | |
| 1-150 | H | OCHF$_2$ | F | F | CF$_3$ | 2 | |
| 1-151 | H | OH | F | F | CF$_3$ | 2 | |
| 1-152 | H | OEt | F | F | CF$_3$ | 2 | |
| 1-153 | H | OCH$_2$—c-Pr | F | F | CF$_3$ | 2 | |
| 1-154 | H | NHCSNH—i-Pr | F | F | CF$_3$ | 2 | |
| 1-155 | H | NHCSNH—i-Pr | F | F | CF$_3$ | 2 | |
| 1-156 | H | 5-Me-Thiazol-2-yl | F | F | CF$_3$ | 2 | |
| 1-157 | H | 5-Me-Isoxazol-3-yl | F | F | CF$_3$ | 2 | |
| 1-158 | H | Bn | F | F | CF$_3$ | 2 | |
| 1-159 | H | 4-F-Bn | F | F | CF$_3$ | 2 | |
| 1-160 | H | 4-CF$_3$-Bn | F | F | CF$_3$ | 2 | |
| 1-161 | H | 4-F-BnO | F | F | CF$_3$ | 2 | |
| 1-162 | H | 4-CF$_3$-BnO | F | F | CF$_3$ | 2 | |
| 1-163 | H | 4-F-BnNH | F | F | CF$_3$ | 2 | |
| 1-164 | H | 4-CF$_3$-BnNH | F | F | CF$_3$ | 2 | |
| 1-165 | H | Pyrrolid-2-one-1-yl | F | F | CF$_3$ | 2 | |
| 1-166 | H | 5,5-Me$_2$-Isoxazolin-3-yl | F | F | CF$_3$ | 2 | |
| 1-167 | 3-F—Ph | H | F | Cl | CF$_3$ | 2 | |
| 1-168 | 3-F—Ph | H | Cl | Cl | CF$_3$ | 2 | |
| 1-169 | 4-F—Ph | H | F | Cl | CF$_3$ | 2 | 185-186 |
| 1-170 | 4-F—Ph | H | Cl | Cl | CF$_3$ | 2 | |
| 1-171 | 3-CF$_3$—Ph | H | F | Cl | CF$_3$ | 2 | 80-81 |
| 1-172 | 3-CF$_3$—Ph | H | Cl | Cl | CF$_3$ | 2 | |

TABLE 1-continued

| | | | | | | | |
|---|---|---|---|---|---|---|---|
| 1-173 | 4-CF$_3$—Ph | H | F | Cl | CF$_3$ | 2 | |
| 1-174 | 4-CF$_3$—Ph | H | Cl | Cl | CF$_3$ | 2 | 164-165 |
| 1-175 | CF$_3$ | H | F | Cl | CF$_3$ | 2 | |
| 1-176 | CF$_3$ | H | Cl | Cl | CF$_3$ | 2 | 174-175 |
| 1-177 | CF$_3$ | H | F | Me | CF$_3$ | 2 | 191-192 |
| 1-178 | CF$_3$ | H | Cl | Me | CF$_3$ | 2 | |
| 1-179 | CF$_3$ | H | Me | Me | CF$_3$ | 2 | |
| 1-180 | I | H | F | Cl | CF$_3$ | 2 | 90-91 |
| 1-181 | I | H | Cl | Cl | CF$_3$ | 2 | 196-197 |
| 1-182 | c-Pr | H | F | Cl | CF$_3$ | 2 | 158-159 |
| 1-183 | c-Pr | H | Cl | Cl | CF$_3$ | 2 | 181-182 |
| 1-184 | 4-Cl—Ph | H | F | F | CF$_3$ | 2 | 194-195 |
| 1-185 | 4-Cl—Ph | H | F | Cl | CF$_3$ | 2 | |
| 1-186 | 4-Cl—Ph | H | Cl | Cl | CF$_3$ | 2 | |
| 1-187 | 4-Br—Ph | H | F | F | CF$_3$ | 2 | |
| 1-188 | 4-Br—Ph | H | F | Cl | CF$_3$ | 2 | |
| 1-189 | 4-Br—Ph | H | Cl | Cl | CF$_3$ | 2 | |
| 1-190 | H | 3-F—Ph | F | Cl | CF$_3$ | 2 | |
| 1-191 | H | 3-F—Ph | Cl | Cl | CF$_3$ | 2 | |
| 1-192 | H | 4-F—Ph | F | Cl | CF$_3$ | 2 | |
| 1-193 | H | 4-F—Ph | Cl | Cl | CF$_3$ | 2 | |
| 1-194 | 3-CF$_3$-Pyrazol-1-yl | H | F | F | CF$_3$ | 2 | 92-94 |
| 1-195 | 3-CF$_3$-Pyrazol-1-yl | H | F | Cl | CF$_3$ | 2 | |
| 1-196 | 3-CF$_3$-Pyrazol-1-yl | H | Cl | Cl | CF$_3$ | 2 | |
| 1-197 | 4-CF$_3$-Pyrazol-1-yl | H | F | F | CF$_3$ | 2 | |
| 1-198 | 4-CF$_3$-Pyrazol-1-yl | H | F | Cl | CF$_3$ | 2 | |
| 1-199 | 4-CF$_3$-Pyrazol-1-yl | H | Cl | Cl | CF$_3$ | 2 | |
| 1-200 | Py-3-yl | H | F | F | CF$_3$ | 2 | 120-121 |
| 1-201 | Py-3-yl | H | F | Cl | CF$_3$ | 2 | |
| 1-202 | Py-3-yl | H | Cl | Cl | CF$_3$ | 2 | 96-97 |
| 1-203 | 2,3-F$_2$—Ph | H | F | F | CF$_3$ | 2 | |
| 1-204 | 2,3-F$_2$—Ph | H | F | Cl | CF$_3$ | 2 | |
| 1-205 | 2,3-F$_2$—Ph | H | Cl | Cl | CF$_3$ | 2 | |
| 1-206 | 2,5-F$_2$—Ph | H | F | F | CF$_3$ | 2 | |
| 1-207 | 2,5-F$_2$—Ph | H | F | Cl | CF$_3$ | 2 | |
| 1-208 | 2,5-F$_2$—Ph | H | Cl | Cl | CF$_3$ | 2 | |
| 1-209 | 3,5-F$_2$—Ph | H | F | F | CF$_3$ | 2 | 134-135 |
| 1-210 | 3,5-F$_2$—Ph | H | F | Cl | CF$_3$ | 2 | 200-201 |
| 1-211 | 3,5-F$_2$—Ph | H | Cl | Cl | CF$_3$ | 2 | 209-210 |
| 1-212 | Thiophen-3-yl | H | F | F | CF$_3$ | 2 | 203-204 |
| 1-213 | Thiophen-3-yl | H | F | Cl | CF$_3$ | 2 | |
| 1-214 | Thiophen-3-yl | H | Cl | Cl | CF$_3$ | 2 | |
| 1-215 | 2,4-F$_2$—Ph | H | F | F | CF$_3$ | 2 | |
| 1-216 | 2,4-F$_2$—Ph | H | F | Cl | CF$_3$ | 2 | |
| 1-217 | 2,4-F$_2$—Ph | H | Cl | Cl | CF$_3$ | 2 | |
| 1-218 | 3,4-F$_2$—Ph | H | F | F | CF$_3$ | 2 | |
| 1-219 | 3,4-F$_2$—Ph | H | F | Cl | CF$_3$ | 2 | |
| 1-220 | 3,4-F$_2$—Ph | H | Cl | Cl | CF$_3$ | 2 | |
| 1-221 | Ph | H | F | F | CF$_3$ | 2 | |
| 1-222 | Ph | H | F | Cl | CF$_3$ | 2 | |
| 1-223 | Ph | H | Cl | Cl | CF$_3$ | 2 | |
| 1-224 | 2-CF$_3$—Ph | H | F | F | CF$_3$ | 2 | 123-124 |
| 1-225 | 2-CF$_3$—Ph | H | F | Cl | CF$_3$ | 2 | |
| 1-226 | 2-CF$_3$—Ph | H | Cl | Cl | CF$_3$ | 2 | 133-134 |
| 1-227 | 2-F—Ph | H | F | F | CF$_3$ | 2 | |
| 1-228 | 2-F—Ph | H | F | Cl | CF$_3$ | 2 | |
| 1-229 | 2-F—Ph | H | Cl | Cl | CF$_3$ | 2 | |
| 1-230 | 2-OCF$_3$—Ph | H | F | F | CF$_3$ | 2 | |
| 1-231 | 2-OCF$_3$—Ph | H | F | Cl | CF$_3$ | 2 | |
| 1-232 | 2-OCF$_3$—Ph | H | Cl | Cl | CF$_3$ | 2 | |
| 1-233 | 3-OCF$_3$—Ph | H | F | F | CF$_3$ | 2 | |
| 1-234 | 3-OCF$_3$—Ph | H | F | Cl | CF$_3$ | 2 | |
| 1-235 | 3-OCF$_3$—Ph | H | Cl | Cl | CF$_3$ | 2 | |
| 1-236 | 4-OCF$_3$—Ph | H | F | F | CF$_3$ | 2 | |
| 1-237 | 4-OCF$_3$—Ph | H | F | Cl | CF$_3$ | 2 | |
| 1-238 | 4-OCF$_3$—Ph | H | Cl | Cl | CF$_3$ | 2 | |
| 1-239 | 3-Cl—Ph | H | F | F | CF$_3$ | 2 | 152-153 |
| 1-240 | 3-Cl—Ph | H | F | Cl | CF$_3$ | 2 | |
| 1-241 | 3-Cl—Ph | H | Cl | Cl | CF$_3$ | 2 | 145-146 |
| 1-242 | 2-Cl—Ph | H | F | F | CF$_3$ | 2 | |
| 1-243 | 2-Cl—Ph | H | F | Cl | CF$_3$ | 2 | |
| 1-244 | 2-Cl—Ph | H | Cl | Cl | CF$_3$ | 2 | |
| 1-245 | 2-SMe—Ph | H | F | F | CF$_3$ | 2 | |
| 1-246 | 2-SMe—Ph | H | F | Cl | CF$_3$ | 2 | |
| 1-247 | 2-SMe—Ph | H | Cl | Cl | CF$_3$ | 2 | |
| 1-248 | 3-SMe—Ph | H | F | F | CF$_3$ | 2 | |
| 1-249 | 3-SMe—Ph | H | F | Cl | CF$_3$ | 2 | |
| 1-250 | 3-SMe—Ph | H | Cl | Cl | CF$_3$ | 2 | |
| 1-251 | 4-SMe—Ph | H | F | F | CF$_3$ | 2 | |
| 1-252 | 4-SMe—Ph | H | F | Cl | CF$_3$ | 2 | |

TABLE 1-continued

| | | | | | | | | |
|---|---|---|---|---|---|---|---|---|
| 1-253 | 4-SMe—Ph | H | | Cl | Cl | $CF_3$ | 2 | |
| 1-254 | 2-CN—Ph | H | | F | F | $CF_3$ | 2 | |
| 1-255 | 2-CN—Ph | H | | F | Cl | $CF_3$ | 2 | |
| 1-256 | 2-CN—Ph | H | | Cl | Cl | $CF_3$ | 2 | |
| 1-257 | 3-CN—Ph | H | | F | F | $CF_3$ | 2 | 196-197 |
| 1-258 | 3-CN—Ph | H | | F | Cl | $CF_3$ | 2 | |
| 1-259 | 3-CN—Ph | H | | Cl | Cl | $CF_3$ | 2 | |
| 1-260 | 4-CN—Ph | H | | F | F | $CF_3$ | 2 | |
| 1-261 | 4-CN—Ph | H | | F | Cl | $CF_3$ | 2 | |
| 1-262 | 4-CN—Ph | H | | Cl | Cl | $CF_3$ | 2 | |
| 1-263 | Py-4-yl | H | | F | F | $CF_3$ | 2 | |
| 1-264 | Py-4-yl | H | | F | Cl | $CF_3$ | 2 | |
| 1-265 | Py-4-yl | H | | Cl | Cl | $CF_3$ | 2 | |
| 1-266 | Py-2-yl | H | | F | F | $CF_3$ | 2 | |
| 1-267 | Py-2-yl | H | | F | Cl | $CF_3$ | 2 | |
| 1-268 | Py-2-yl | H | | Cl | Cl | $CF_3$ | 2 | |
| 1-269 | Thiophen-2-yl | H | | F | F | $CF_3$ | 2 | |
| 1-270 | Thiophen-2-yl | H | | F | Cl | $CF_3$ | 2 | |
| 1-271 | Thiophen-2-yl | H | | Cl | Cl | $CF_3$ | 2 | |
| 1-272 | 1-Me-Pyrazol-5-yl | H | | F | F | $CF_3$ | 2 | |
| 1-273 | 1-Me-Pyrazol-5-yl | H | | F | Cl | $CF_3$ | 2 | |
| 1-274 | 1-Me-Pyrazol-5-yl | H | | Cl | Cl | $CF_3$ | 2 | |
| 1-275 | Pyrimidin-5-yl | H | | F | F | $CF_3$ | 2 | |
| 1-276 | Pyrimidin-5-yl | H | | F | Cl | $CF_3$ | 2 | |
| 1-277 | Pyrimidin-5-yl | H | | Cl | Cl | $CF_3$ | 2 | |
| 1-278 | Benzofuran-2-yl | H | | F | F | $CF_3$ | 2 | |
| 1-279 | Benzofuran-2-yl | H | | F | Cl | $CF_3$ | 2 | |
| 1-280 | Benzofuran-2-yl | H | | Cl | Cl | $CF_3$ | 2 | |
| 1-281 | Benzothiophen-2-yl | H | | F | F | $CF_3$ | 2 | |
| 1-282 | Benzothiophen-2-yl | H | | F | Cl | $CF_3$ | 2 | |
| 1-283 | Benzothiophen-2-yl | H | | Cl | Cl | $CF_3$ | 2 | |
| 1-284 | 2-Me-Thiazol-4-yl | H | | F | F | $CF_3$ | 2 | |
| 1-285 | 2-Me-Thiazol-4-yl | H | | F | Cl | $CF_3$ | 2 | |
| 1-286 | 2-Me-Thiazol-4-yl | H | | Cl | Cl | $CF_3$ | 2 | |
| 1-287 | $OCH_2CF_3$ | H | | F | F | $CF_3$ | 2 | 149-150 |
| 1-288 | $OCH_2CF_3$ | H | | Cl | Cl | $CF_3$ | 2 | |
| 1-289 | $OCH_2CF_3$ | H | | F | Cl | $CF_3$ | 2 | |
| 1-290 | OEt | H | | Cl | Cl | $CF_3$ | 2 | 215-217 |
| 1-291 | OEt | H | | F | Cl | $CF_3$ | 2 | |
| 1-292 | O—i-Pr | H | | F | Cl | $CF_3$ | 2 | |
| 1-293 | 4-$CF_3$-BnO | H | | Cl | Cl | $CF_3$ | 2 | |
| 1-294 | 3-$CF_3$-BnO | H | | F | F | $CF_3$ | 2 | |
| 1-295 | 3-$CF_3$-BnO | H | | Cl | Cl | $CF_3$ | 2 | |
| 1-296 | 3-Cl-BnO | H | | F | F | $CF_3$ | 2 | |
| 1-297 | 3-Cl-BnO | H | | Cl | Cl | $CF_3$ | 2 | |
| 1-298 | 4-Cl-BnO | H | | F | F | $CF_3$ | 2 | |
| 1-299 | 4-Cl-BnO | H | | Cl | Cl | $CF_3$ | 2 | |
| 1-300 | 2-Cl-BnO | H | | F | F | $CF_3$ | 2 | |
| 1-301 | 2-Cl-BnO | H | | Cl | Cl | $CF_3$ | 2 | |

$A^1$ and $A^3$ each represent a nitrogen atom, $A^2$ represents CH, $R^1$ represents an ethyl group, and $R^2$ represents a hydrogen atom.

[Chem. 5]

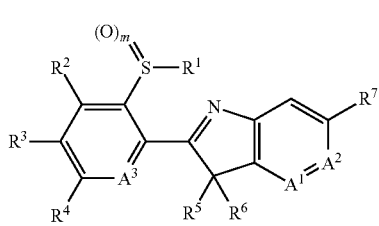

(1)

TABLE 2

| Compound No. | $R^3$ | $R^4$ | $R^5$ | $R^6$ | $R^7$ | m | Physical property |
|---|---|---|---|---|---|---|---|
| 2-1 | $CF_3$ | H | F | F | $CF_3$ | 2 | 135-136 |
| 2-2 | $CF_3$ | H | F | Cl | $CF_3$ | 2 | |
| 2-3 | $CF_3$ | H | Cl | Cl | $CF_3$ | 2 | NMR |
| 2-4 | I | H | F | F | $CF_3$ | 2 | |
| 2-5 | I | H | F | Cl | $CF_3$ | 2 | |
| 2-6 | I | H | Cl | Cl | $CF_3$ | 2 | |
| 2-7 | c-Pr | H | F | F | $CF_3$ | 2 | |
| 2-8 | c-Pr | H | F | Cl | $CF_3$ | 2 | |
| 2-9 | c-Pr | H | Cl | Cl | $CF_3$ | 2 | |
| 2-10 | 3-F—Ph | H | F | F | $CF_3$ | 2 | |
| 2-11 | 3-F—Ph | H | F | Cl | $CF_3$ | 2 | |
| 2-12 | 3-F—Ph | H | Cl | Cl | $CF_3$ | 2 | |
| 2-13 | 4-F—Ph | H | F | F | $CF_3$ | 2 | 218-219 |
| 2-14 | 4-F—Ph | H | F | Cl | $CF_3$ | 2 | |
| 2-15 | 4-F—Ph | H | Cl | Cl | $CF_3$ | 2 | |
| 2-16 | 3-$CF_3$—Ph | H | F | F | $CF_3$ | 2 | 170-171 |
| 2-17 | 3-$CF_3$—Ph | H | F | Cl | $CF_3$ | 2 | |
| 2-18 | 3-$CF_3$—Ph | H | Cl | Cl | $CF_3$ | 2 | |
| 2-19 | 4-$CF_3$—Ph | H | F | F | $CF_3$ | 2 | |
| 2-20 | 4-$CF_3$—Ph | H | F | Cl | $CF_3$ | 2 | |
| 2-21 | 4-$CF_3$—Ph | H | Cl | Cl | $CF_3$ | 2 | |
| 2-22 | 3-$CF_3$-Pyrazol-1-yl | H | F | F | $CF_3$ | 2 | |
| 2-23 | 3-$CF_3$-Pyrazol-1-yl | H | F | Cl | $CF_3$ | 2 | |
| 2-24 | 3-$CF_3$-Pyrazol-1-yl | H | Cl | Cl | $CF_3$ | 2 | |

$A^3$ represents a nitrogen atom, $A^1$ and $A^2$ each represent CH, $R^1$ represents an ethyl group, and $R^2$ represents a hydrogen atom.

[Chem. 6]

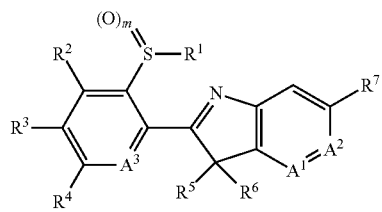

(1)

TABLE 3

| Compound No. | R³ | R⁴ | R⁵ | R⁶ | R⁷ | m | Physical property |
|---|---|---|---|---|---|---|---|
| 3-1 | I | H | F | F | CF₃ | 2 | |
| 3-2 | I | H | F | Cl | CF₃ | 2 | |
| 3-3 | I | H | Cl | Cl | CF₃ | 2 | |
| 3-4 | c-Pr | H | F | F | CF₃ | 2 | |
| 3-5 | c-Pr | H | F | Cl | CF₃ | 2 | |
| 3-6 | c-Pr | H | Cl | Cl | CF₃ | 2 | |
| 3-7 | 3-F—Ph | H | F | F | CF₃ | 2 | |
| 3-8 | 3-F—Ph | H | F | Cl | CF₃ | 2 | |
| 3-9 | 3-F—Ph | H | Cl | Cl | CF₃ | 2 | |
| 3-10 | 4-F—Ph | H | F | F | CF₃ | 2 | |
| 3-11 | 4-F—Ph | H | F | Cl | CF₃ | 2 | |
| 3-12 | 4-F—Ph | H | Cl | Cl | CF₃ | 2 | |
| 3-13 | 3-CF₃—Ph | H | F | F | CF₃ | 2 | |
| 3-14 | 3-CF₃—Ph | H | F | Cl | CF₃ | 2 | |
| 3-15 | 3-CF₃—Ph | H | Cl | Cl | CF₃ | 2 | |
| 3-16 | 4-CF₃—Ph | H | F | F | CF₃ | 2 | |
| 3-17 | 4-CF₃—Ph | H | F | Cl | CF₃ | 2 | |
| 3-18 | 4-CF₃—Ph | H | Cl | Cl | CF₃ | 2 | |

$A^1$ represents a nitrogen atom, $A^2$ and $A^3$ each represent CH, $R^1$ represents an ethyl group, and $R^2$ represents a hydrogen atom.

TABLE 4

¹H-NMR data

| Compound No. | ¹H-NMR data |
|---|---|
| 1-4 | 8.83 (1H, s), 8.50 (1H, s), 8.10 (1H, s), 8.09 (1H, d), 3.60 (2H, dd), 1.38 (3H, t) |
| 1-5 | 9.36 (1H, s), 8.98 (1H, s), 8.87 (1H, d), 8.26 (1H, d), 3.95-3.83 (2H, m), 1.44 (3H, t) |
| 1-6 | 9.17 (1H, s), 8.90 (1H, s), 8.85 (1H, d), 8.21 (1H, d), 4.07-3.87 (2H, m), 3.83 (3H, s), 1.45 (3H, t) |
| 1-7 | 9.08 (1H, s), 8.90 (1H, s), 8.85 (1H, d), 8.25 (1H, s), 3.84 (3H, s), 3.37-3.31 (1H, m), 2.94-2.89 (1H, m), 1.37 (3H, t) |
| 1-8 | 9.08 (1H, s), 8.90 (1H, s), 8.85 (1H, d), 8.21 (1H, s), 3.84 (3H, s), 3.50-3.45 (1H, m), 3.02-2.97 (1H, m), 1.46 (3H, t) |
| 1-9 | 9.20 (1H, s), 8.92 (1H, s), 8.19 (1H, d), 8.26 (1H, d), 3.42-3.34 (1H, m), 2.99-2.90 (1H, m), 1.41 (3H, t) |
| 1-10 | 9.29 (1H, s), 8.92 (1H, s), 8.80 (1H, s), 8.14 (1H, s), 3.80 (2H, dd), 1.43 (3H, t) |
| 2-3 | 9.28 (1H, d), 8.83 (1H, d), 8.90 (1H, s), 8.89 (1H, d), 7.79 (1H, d), 3.93 (2H, q), 1.44 (3H, t) |

The agricultural and horticultural insecticide comprising the condensed heterocyclic compound represented by the general formula (1) of the present invention, an oxide thereof or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, nematodes, etc.

Specific examples of the pests, nematodes, etc. include the following:

the species of the order Lepidoptera such as *Parasa consocia*, *Anomis mesogona*, *Papilio xuthus*, *Matsumuraeses azukivora*, *Ostrinia scapulalis*, *Spodoptera exempta*, *Hyphantria cunea*, *Ostrinia furnacalis*, *Pseudaletia separata*, *Tinea translucens*, *Bactra furfurana*, *Parnara guttata*, *Marasmia exigua*, *Parnara guttata*, *Sesamia inferens*, *Brachmia triannulella*, *Monema flavescens*, *Trichoplusia ni*, *Pleuroptya ruralis*, *Cystidia couaggaria*, *Lampides boeticus*, *Cephonodes hylas*, *Helicoverpa armigera*, *Phalerodonta manleyi*, *Eumeta japonica*, *Pieris brassicae*, *Malacosoma neustria testacea*, *Stathmopoda masinissa*, *Cuphodes diospyrosella*, *Archips xylosteanus*, *Agrotis segetum*, *Tetramoera schistaceana*, *Papilio machaon hippocrates*, *Endoclyta sinensis*, *Lyonetia prunifoliella*, *Phyllonorycter ringoneella*, *Cydia kurokoi*, *Eucoenogenes aestuosa*, *Lobesia botrana*, *Latoia sinica*, *Euzophera batangensis*, *Phalonidia mesotypa*, *Spilosoma imparilis*, *Glyphodes pyloalis*, *Olethreutes mori*, *Tineola bisselliella*, *Endoclyta excrescens*, *Nemapogon granellus*, *Synanthedon hector*, *Cydia pomonella*, *Plutella xylostella*, *Cnaphalocrocis medinalis*,

*Sesamia calamistis*, *Scirpophaga incertulas*, *Pediasia teterrellus*, *Phthorimaea operculella*, *Stauropus fagi persimilis*, *Etiella zinckenella*, *Spodoptera exigua*, *Palpifer sexnotata*, *Spodoptera mauritia*, *Scirpophaga innotata*, *Xestia c-nigrum*, *Spodoptera depravata*, *Ephestia kuehniella*, *Angerona prunaria*, *Clostera anastomosis*, *Pseudoplusia includens*, *Matsumuraeses falcana*, *Helicoverpa assulta*, *Autographa nigrisigna*, *Agrotis ipsilon*, *Euproctis pseudoconspersa*, *Adoxophyes orana*, *Caloptilia theivora*, *Homona magnanima*, *Ephestia elutella*, *Eumeta minuscula*, *Clostera anachoreta*, *Heliothis maritima*, *Sparganothis pilleriana*, *Busseola fusca*, *Euproctis subflava*, *Biston robustum*, *Heliothis zea*, *Aedia leucomelas*, *Narosoideus flavidorsalis*, *Viminia rumicis*, *Bucculatrix pyrivorella*, *Grapholita molesta*, *Spulerina astaurota*, *Ectomyelois pyrivorella*,

*Chilo suppressalis*, *Acrolepiopsis sapporensis*, *Plodia interpunctella*, *Hellula undalis*, *Sitotroga cerealella*, *Spodoptera litura*, a species of the family Tortricidae (*Eucosma aporema*), *Acleris comariana*, *Scopelodes contractus*, *Orgyia thyellina*, *Spodoptera frugiperda*, *Ostrinia zaguliaevi*, *Naranga aenescens*, *Andraca bipunctata*, *Paranthrene regalis*, *Acosmeryx castanea*, *Phyllocnistis toparcha*, *Endopiza viteana*, *Eupoecillia ambiguella*, *Anticarsia gemmatalis*, *Cnephasia cinereipalpana*,

*Lymantria dispar*, *Dendrolimus spectabilis*, *Leguminivora glycinivorella*, *Maruca testulalis*, *Matsumuraeses phaseoli*, *Caloptilia soyella*, *Phyllocnistis citrella*, *Omiodes indicata*,

*Archips fuscocupreanus, Acanthoplusia agnata, Bambalina* sp., *Carposina niponensis, Conogethes punctiferalis, Synanthedon* sp., *Lyonetia clerkella, Papilio helenus, Colias erate poliographus, Phalera flavescens*, the species of the family Pieridae such as *Pieris rapae crucivora* and *Pieris rapae, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens* and *Earias cupreoviridis;* the species of the order Hemiptera such as *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophum rufiabdominalis, Saissetia oleae, Trialeurodes vaporariorum, Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatella, Eurydema pulchrum, Cletus trigonus, Clovia punctata, Empoasca* sp., *Coccus hesperidum, Pachybrachius luridus, Planococcus kraunhiae, Stenotus binotatus, Arboridia apicalis, Macros teles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii;* the species of the order Coleoptera such as *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Eucepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris qua tuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis;* the species of the order Diptera such as *Culex pipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans*, the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes*

*albopictus, Liriomyza trifolii, Liriomyza sativae, Dacus dorsalis, Dacus tsuneonis, Sitodiplosis mosellana, Meromuza nigriventris, Anastrepha ludens* and *Rhagoletis pomonella;*
the species of the order Hymenoptera such as *Pristomyrmex pungens,* the species of the family Bethylidae, *Monomorium pharaonis, Pheidole noda, Athalia rosae, Dryocosmus kuriphilus, Formica fusca japonica,* the species of the subfamily Vespinae, *Athalia infumata infumata, Arge pagana, Athalia japonica, Acromyrmex* spp., *Solenopsis* spp., *Arge mali* and *Ochetellus glaber;*
the species of the order Orthoptera such as *Homorocoryphus lineosus, Gryllotalpa* sp., *Oxya hyla intricata, Oxya yezoensis, Locusta migratoria, Oxya japonica, Homorocoryphus jezoensis* and *Teleogryllus emma;*
the species of the order Thysanoptera such as *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Franklinella occidentalis, Thrips palmi, Frankliniella lilivora* and *Liothrips vaneeckei;*
the species of the order Acari such as *Leptotrombidium akamushi, Tetranychus ludeni, Dermacentor variabilis, Tetranychus truncatus, Ornithonyssus bacoti, Demodex canis, Tetranychus viennensis, Tetranychus kanzawai,* the species of the family Ixodidae such as *Rhipicephalus sanguineus, Cheyletus malaccensis, Tyrophagus putrescentiae, Dermatophagoides farinae, Latrodectus hasseltii, Dermacentor taiwanicus, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.;
the species of the order Isoptera such as *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei* and *Reticulitermes speratus;*
the species of the order Blattodea such as *Periplaneta fuliginosa, Blattella germanica, Blatta orientalis, Periplaneta brunnea, Blattella lituricollis, Periplaneta japonica* and *Periplaneta americana;*
the species of the order Siphonaptera such as *Pulex irritans, Ctenocephalides felis* and *Ceratophyllus gallinae;*
the species of the phylum Nematoda such as *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and *Tylenchus semipenetrans;* the species of the phylum Mollusca such as *Pomacea canaliculata, Achatina fulica, Meghimatium bilineatum, Lehmannina valentiana, Limax flavus* and *Acusta despecta sieboldiana.*

In addition, the agricultural and horticultural insecticide of the present invention has a strong insecticidal effect on *Tuta absoluta* as well.

Further, mites and ticks parasitic on animals are also included in the target pests, and the examples include the species of the family Ixodidae such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanesis; Dermanyssus gallinae*; the species of the genus *Ornithonyssus* such as *Ornithonyssus sylviarum* and *Ornithonyssus bursa*; the species of the family Trombiculidae such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi* and *Helenicula miyagawai*; the species of the family Cheyletidae such as *Cheyletiella yasguri, Cheyletiella parasitivorax* and *Cheyletiella blakei*; the species of the superfamily Sarcoptoidea such as *Psoroptes cuniculi, Chorioptes bovis, Otodectes cynotis, Sarcoptes scabiei* and *Notoedres cati*; and the species of the family Demodicidae such as *Demodex canis.*

Other target pests include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Mosopsyllus anisus.*

Other target pests include ectoparasites, for example, the species of the suborder Anoplura such as *Haematopinus eurysternus, Haematopinus asini, Dalmalinia ovis, Linognathus vituli, Haematopinus suis, Phthirus pubis* and *Pediculus capitis*; the species of the suborder Mallophaga such as *Trichodectes canis*; and hematophagous Dipteran insect pests such as *Tabanus trigonus, Culicoides schultzei* and *Simulium ornatum.* Also included are endoparasites, for example, nematodes such as lungworms, whipworms, nodular worms, endogastric parasitic worms, ascarides and filarial worms; cestodes such as *Spirometra erinacei, Diphyllobothrium latum, Dipylidium caninum, Multiceps multiceps, Echinococcus granulosus* and *Echinococcus multilocularis*; trematodes such as *Schistosoma japonicum* and *Fasciola hepatica*; and protozoa such as coccidia, *Plasmodium,* intestinal *Sarcocystis, Toxoplasma* and *Cryptosporidium.*

The agricultural and horticultural insecticide comprising the condensed heterocyclic compound represented by general formula (1) of the present invention or a salt thereof as an active ingredient has a remarkable control effect on the above-described pests which damage lowland crops, field crops, fruit trees, vegetables, other crops, ornamental flowering plants, etc. The desired effect can be obtained when the agricultural and horticultural insecticide is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticide utilizes so-called penetration and translocation. That is, nursery soil, soil in transplanting holes, plant foot, irrigation water, cultivation water in hydroponics, or the like is treated with the agricultural and horticultural insecticide to allow crops, ornamental flowering plants, etc. to absorb the compound of the present invention through the roots via soil or otherwise.

Examples of useful plants to which the agricultural and horticultural insecticide of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., chrysanthemum, rose, carnation, orchid, tulip, lily, etc.), garden trees (e.g., ginkgo trees, cherry trees, Japanese aucuba, etc.) and forest trees (e.g., *Abies sachalinensis*, *Picea jezoensis*, pine, yellow cedar, Japanese cedar, hinoki cypress, eucalyptus, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticide of the present invention can be applied to these plants as well.

Further, exemplary toxins expressed in genetically modified plants include insecticidal proteins of *Bacillus cereus* or *Bacillus popilliae*; *Bacillus thuringiensis* δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticide of the present invention can be used in combination or used systematically.

In order to control target pests, the agricultural and horticultural insecticide of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots.

Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticide of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of a solid or liquid formulation and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer or the like, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticide of the present invention is commonly used as a formulation convenient for application, which is prepared in the usual method for preparing agrochemical formulations.

That is, the condensed heterocyclic compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticide or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, or two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, or two or more of them may be used in combination.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, or two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, or two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural and horticultural insecticide of the present invention can be adjusted as needed, and basically, the amount of the active ingredient compound is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural and horticultural insecticide).

The application rate of the agricultural and horticultural insecticide of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Furthermore, for the expansion of the range of target pests and the appropriate time for pest control, or for dose reduction, the agricultural and horticultural insecticide of the present invention can be used after mixed with other agricultural and horticultural insecticides, acaricides, nematicides, microbicides, biopesticides and/or the like. Further, the agricultural and horticultural insecticide can be used after mixed with herbicides, plant growth regulators, fertilizers and/or the like depending on the situation.

Examples of such additional agricultural and horticultural insecticides, acaricides and nematicides used for the above-mentioned purposes include 3,5-xylyl methylcarbamate (XMC), crystalline protein toxins produced by *Bacillus thuringiensis* such as *Bacillus thuringiensis aizawai, Bacillus thuringiensis israelensis, Bacillus thuringiensis japonensis, Bacillus thuringiensis kurstaki* and *Bacillus thuringiensis tenebrionis*, BPMC, Bt toxin-derived insecticidal compounds, chlorfenson (CPCBS), dichlorodiisopropyl ether (DCIP), 1,3-dichloropropene (D-D), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetrametrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Examples of the agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloranimethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bisethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Further, examples of the herbicides include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ephephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam,
hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Examples of the biopesticides include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as *Monacrosporium phymatophagum, Steinernema carpocapsae, Steinernema kushidai* and *Pasteuria penetrans*; microbial pesticides used as a microbicide, such as *Trichoderma lignorum, Agrobacterium radiobactor*, avirulent *Erwinia carotovora* and *Bacillus subtilis*; and biopesticides used as a herbicide, such as *Xanthomonas campestris*. A combined use of the agricultural and horticultural insecticide of the present invention with the foregoing biopesticide as a mixture can be expected to provide the same effect as above.

Other examples of the biopesticides include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

The compounds of the present invention have excellent biological characteristics as described above, and in addition, have low environmental burden, as exemplified by being easily degradable in the environment and having less impact on useful organisms such as honeybees.

Hereinafter, the production examples of representative compounds of the present invention and their intermediates will be described in more detail, but the present invention is not limited only to these examples.

EXAMPLES

Reference Example 1

Production Method of 1-Trimethylsilyl-2-(2-ethyl-thio-4-trifluoromethylphenyl)ethyne

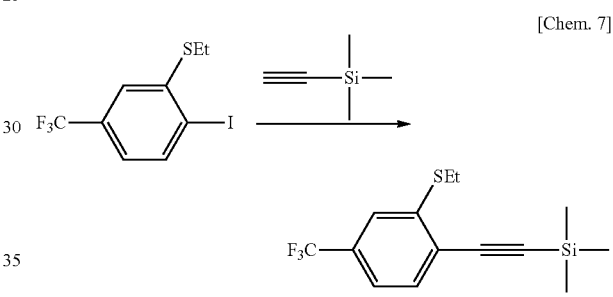

[Chem. 7]

2-Ethylthio-4-trifluoromethyl iodobenzene (3 g) was mixed with tetrahydrofuran (5 mL), triethylamine (2 mL), trimethylsilylacetylene (1.3 g), bistriphenylphosphine dichloropalladium (315 mg), copper iodide (171 mg) and triphenylphosphine (118 mg), and the mixture was heated under argon at 40° C. with stirring for 2 hours. The reaction mixture was concentrated in vacuo and the resulting residue was subjected to column chromatography to give the desired compound (3.2 g).

Physical property: $^1$H-NMR (CDCl$_3$): 7.92 (d, 1H), 7.34 (d, 1H), 7.07 (dd, 1H), 2.99 (dd, 2H), 1.42 (t, 3H), 0.29 (s, 9H)

Reference Example 2

Production Method of 2-(2-Ethylthio-4-trifluoromethylphenyl)-6-trifluoromethyl-1H-pyrrolo[3,2-b]pyridine

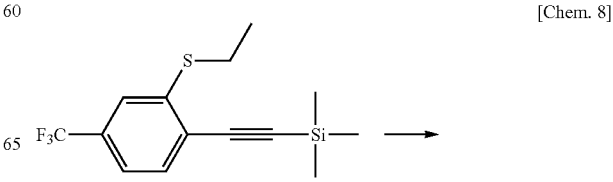

[Chem. 8]

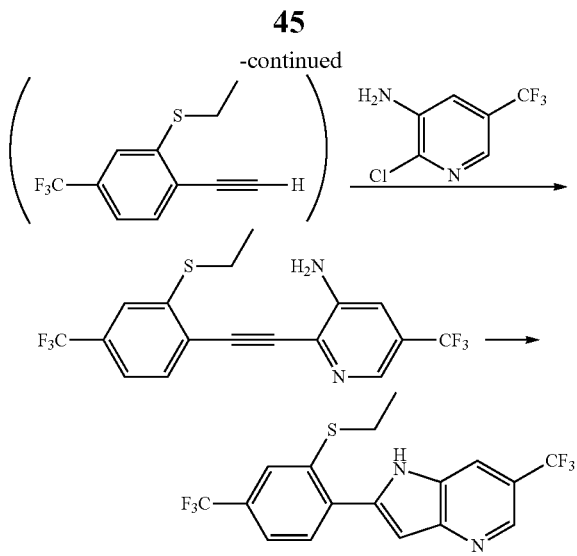

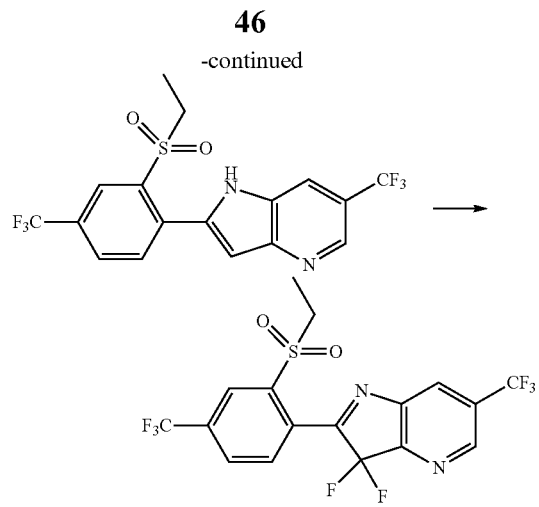

1-Trimethylsilyl-2-(2-ethylthio-4-trifluoromethylphenyl)ethyne (794 mg), 3-amino-2-chloro-5-trifluoromethylpyridine (650 mg, 1.1 Eq), triethylamine (1 mL), diphenylphosphino ferrocene dichloropalladium (141 mg), copper iodide (33 mg), DMF (5 mL) and a 1 M THF (tetrahydrofuran) solution (4 mL) of tetrabutylammonium fluoride were mixed, and the mixture was heated at reflux under argon for 4 hours. The reaction mixture was concentrated and the resulting residue was subjected to column chromatography to give the desired compound, i.e., 2-(2-ethylthio-4-trifluoromethylphenyl)ethynyl-5-trifluoromethylpyridin-3-amine (0.54 g). The obtained compound was dissolved in DMF (3 mL), potassium t-butoxide (672 mg, 3 Eq) was added to the solution, and the mixture was heated at 100° C. with stirring for 3 hours. After the reaction mixture was allowed to cool down to room temperature, silica gel was added and the mixture was concentrated. The residue was subjected to column chromatography to give 2-(2-ethylthio-4-trifluoromethylphenyl)-6-trifluoromethyl-1H-pyrrolo[3,2-b]pyridine.

The 2-(2-ethylthio-4-trifluoromethylphenyl)-6-trifluoromethyl-1H-pyrrolo[3,2-b]pyridine (218 mg, 0.559 mmol) produced in Reference Example 2 was dissolved in ethyl acetate (3 mL) and chloroform (10 mL). m-Perbenzoic acid (745 mg, 5 Eq) was added to the solution, and the mixture was stirred at room temperature for 1 hour. After that, water, potassium carbonate and ethyl acetate were added, and ethyl acetate extraction was performed 3 times. After the organic layer was concentrated, chloroform (10 mL) and phosphorus trichloride (822 mg, 10 Eq) were added to the residue, and the mixture was exposed to ultrasonication at room temperature for 5 minutes. After that, water, potassium carbonate and ethyl acetate were added, and ethyl acetate extraction was performed 3 times. The organic layer was dried over sodium sulfate and then concentrated. The residue was subjected to column chromatography to give 2-(2-ethylsulfonyl-4-trifluoromethylphenyl)-6-trifluoromethyl-1H-pyrrolo[3,2-b]pyridine. The obtained compound (110 mg, 0.258 mmol), sodium bicarbonate (65 mg, 3 Eq) and water (28 mg, 6 Eq) were dissolved in acetonitrile (5 mL). Subsequently, Selectfluor (274 mg, 3 Eq) was added and the mixture was stirred at room temperature for 3 hours. After the completion of the reaction, water and ethyl acetate were added, and ethyl acetate extraction was performed 3 times. The organic layer was dried over sodium sulfate and then concentrated. The residue was subjected to column chromatography to give 2-(2-ethylthio-4-trifluoromethylphenyl)-3,3-difluoro-6-trifluoromethyl-3H-pyrrolo[3,2-b]pyridine.

Physical property: 120 to 122° C.

Reference Example 3

Production Method of 2-Methyl-1-phenylpropan-2-yl 3-(3-ethylthio-5-trifluoromethylpyridin-2-yl)-2-(3-nitro-5-trifluoromethylpyridin-2-yl)-3-oxo-propionate Example 1

Production Method of 2-(2-Ethylthio-4-trifluoromethylphenyl)-3,3-difluoro-6-trifluoromethyl-3H-pyrrolo[3,2-b]pyridine (Compound number 1-1)

[Chem. 9]

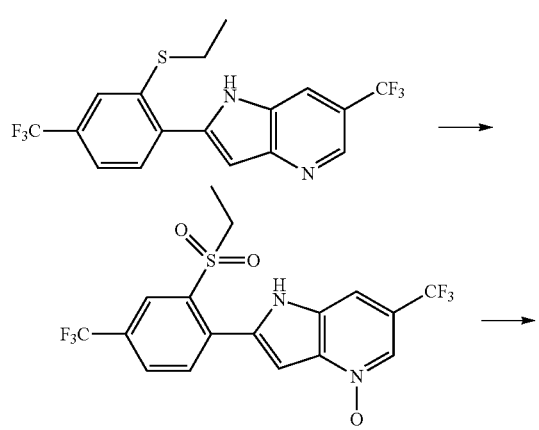

[Chem. 10]

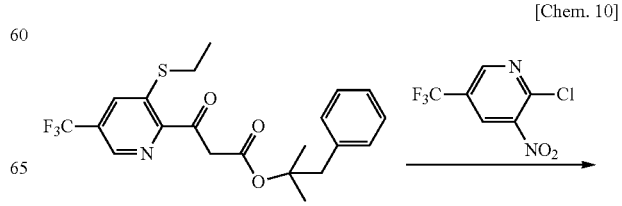

-continued

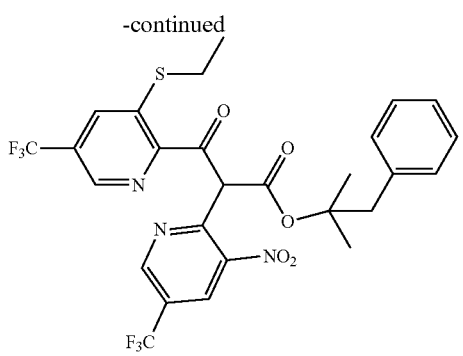

Sodium hydride (240 mg, 3 Eq) was dissolved in DMA (dimethylacetamide) (2 mL). Under ice cooling, a DMA solution (2 mL) of 2-methyl-1-phenylpropan-2-yl 3-(3-ethylthio-5-trifluoromethylpyridin-2-yl)-3-oxo-propionate (895 mg, 2 mmol) was slowly added to the solution, and the mixture was stirred for 30 minutes. After that, a DMA solution (2 mL) of 2-chloro-3-nitro-5-trifluoromethylpyridine (454 mg, 1 Eq) was slowly added, and the mixture was stirred at room temperature for 4.5 hours. Water and 3 N hydrochloric acid were added to the reaction mixture, and ethyl acetate extraction was performed. The organic layer was concentrated and the residue was subjected to column chromatography to give the desired compound, i.e., 2-methyl-1-phenylpropan-2-yl 3-(3-ethylthio-5-trifluoromethylpyridin-2-yl)-2-(3-nitro-5-trifluoromethylpyridin-2-yl)-3-oxo-propionate (653 mg, containing about 20% nitropyridine (starting material)).

Reference Example 4

Production Method of 1-(3-Ethylthio-5-trifluoromethylpyridin-2-yl)-2-(3-nitro-5-trifluoromethylpyridin-2-yl)ethanone

[Chem. 11]

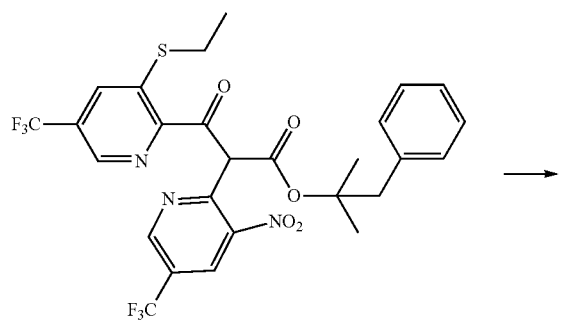

2-Methyl-1-phenylpropan-2-yl 3-(3-ethylthio-5-trifluoromethylpyridin-2-yl)-2-(3-nitro-5-trifluoromethylpyridin-2-yl)-3-oxo-propionate (653 mg, ca. 0.4 mmol) was dissolved in trifluoroacetic acid (5 mL), and the solution was heated at 80° C. with stirring for 0.5 hour. The reaction mixture was concentrated and the residue was subjected to column chromatography to give the desired compound, i.e., 1-(3-ethylthio-5-trifluoromethylpyridin-2-yl)-2-(3-nitro-5-trifluoromethylpyridin-2-yl)ethanone (172 mg, 98%).

Reference Example 5

Production Method of 2-(3-Ethylthio-5-trifluoromethylpyridin-2-yl)-6-trifluoromethyl-1H-pyrrolo[3,2-b]pyridine

[Chem. 12]

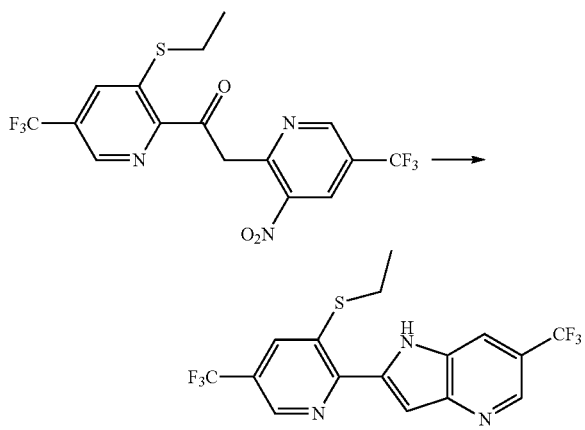

To 1-(3-ethylthio-5-trifluoromethylpyridin-2-yl)-2-(3-nitro-5-trifluoromethylpyridin-2-yl)ethanone (171 mg, 0.39 mmol), acetic acid (5 mL) and iron powder (109 mg, 5 Eq) were added, and the mixture was stirred at 80° C. for 1 hour. After the reaction mixture was allowed to cool down to room temperature, water and ethyl acetate were added, and ethyl acetate extraction was performed 3 times. The organic layer was concentrated and the residue was subjected to column chromatography to give the desired compound, i.e., 2-(3-ethylthio-5-trifluoromethylpyridin-2-yl)-6-trifluoromethyl-1H-pyrrolo[3,2-b]pyridine (98 mg, 65%).

Example 2

Production Method of 2-(3-Ethylsulfinyl-5-trifluoromethylpyridin-2-yl)-3,3-difluoro-6-trifluoromethyl-3H-pyrrolo[3,2-b]pyridine (Compound number 1-9) and 2-(3-Ethylsulfonyl-5-trifluoromethylpyridin-2-yl)-3,3-difluoro-6-trifluoromethyl-3H-pyrrolo[3,2-b]pyridine (Compound number 1-10)

[Chem. 13]

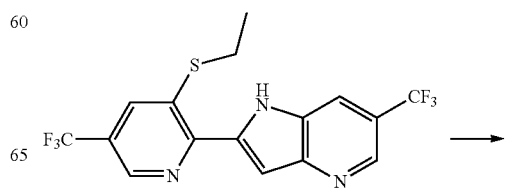

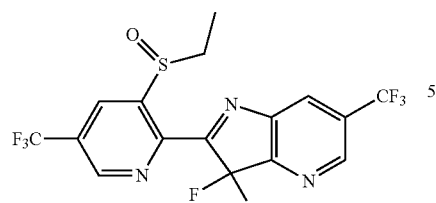

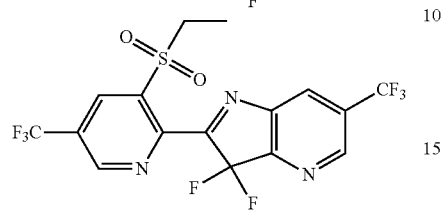

2-(3-Ethylthio-5-trifluoromethylpyridin-2-yl)-6-trifluoromethyl-1H-pyrrolo[3,2-b]pyridine (98 mg, 0.25 mmol), sodium bicarbonate (126 mg, 6 Eq), water (54 mg, 12 Eq), acetonitrile (3 mL) and Selectfluor (531 mg, 6 Eq) were mixed and then stirred at room temperature for 1 hour. Silica gel was added to the reaction system and the mixture was concentrated. The residue was subjected to column chromatography to give the desired sulfoxide compound (26.4 mg, 28%) and the desired sulfone compound (39.3 mg, 40%).

Reference Example 6

Production Method of 2-(3-Ethylthio-5-iodopyridin-2-yl)-1-tert-butoxycarbonyl-6-trifluoromethyl-1H-pyrrolo[3,2-b]pyridine

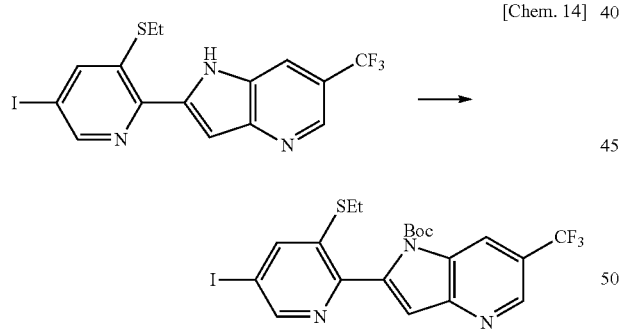

[Chem. 14]

To a THF solution (40 mL) of 2-(3-ethylthio-5-iodopyridin-2-yl)-6-trifluoromethyl-1H-pyrrolo[3,2-b]pyridine (4.0 g), which had been produced according to the same scheme as described in Reference Examples 3 to 5, DMAP (4-dimethylaminopyridine) (0.25 g) and Boc$_2$O (2.6 mL) were added, and the mixture was stirred at room temperature overnight. After the completion of the reaction, a saturated aqueous sodium bicarbonate solution was added, and ethyl acetate extraction was performed. The organic layer was dried over anhydrous magnesium sulfate and then dried in vacuo, and the residue was purified by silica gel chromatography to give the desired compound (4.8 g, quantitative). Boc stands for tert-butoxycarbonyl.

Reference Example 7

Production Method of 2-(3-Ethylsulfonyl-5-iodopyridin-2-yl)-1-tert-butoxycarbonyl-6-trifluoromethyl-1H-pyrrolo[3,2-b]pyridine

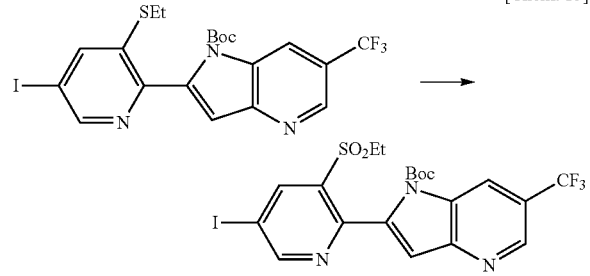

[Chem. 15]

To an ethyl acetate solution (74 mL) of the 2-(3-ethylthio-5-iodopyridin-2-yl)-1-tert-butoxycarbonyl-6-trifluoromethyl-1H-pyrrolo[3,2-b]pyridine (4.1 g) produced in the previous step, m-chloroperoxybenzoic acid (4.2 g) was added at room temperature, and the mixture was stirred for 2 hours. After the completion of the reaction, a saturated aqueous sodium bicarbonate solution and a saturated aqueous sodium thiosulfate solution were added, and ethyl acetate extraction was performed. The organic layer was washed with a saturated aqueous sodium bicarbonate solution, dried over anhydrous magnesium sulfate and then dried in vacuo. The residue was purified by silica gel chromatography to give the desired compound (3.2 g, 72%).

Reference Example 8

Production Method of 2-(3-Ethylsulfonyl-5-(4-fluorophenyl)pyridin-2-yl)-1-tert-butoxycarbonyl-6-trifluoromethyl-1H-pyrrolo[3,2-b]pyridine

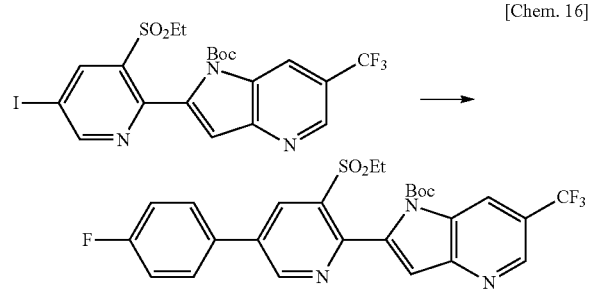

[Chem. 16]

To a DME (1,2-dimethoxyethane)/H$_2$O (4:1) solution (2 mL) of the 2-(3-ethylsulfonyl-5-iodopyridin-2-yl)-1-tert-butoxycarbonyl-6-trifluoromethyl-1H-pyrrolo[3,2-b]pyridine (0.13 g) produced in the previous step, 4-fluorophenylboronic acid (0.047 g), PdCl$_2$ (dppf).acetone (0.008 g) and Cs$_2$CO$_3$ (0.21 g) were added, and the mixture was heated at reflux for 1 hour. After the completion of the reaction, the reaction mixture was dried in vacuo, and the residue was purified by silica gel chromatography to give the desired compound. This product was subjected to the next step without purification.

Reference Example 9

Production Method of 2-(3-Ethylsulfonyl-5-(4-fluorophenyl)pyridin-2-yl)-6-trifluoromethyl-1H-pyrrolo[3,2-b]pyridine

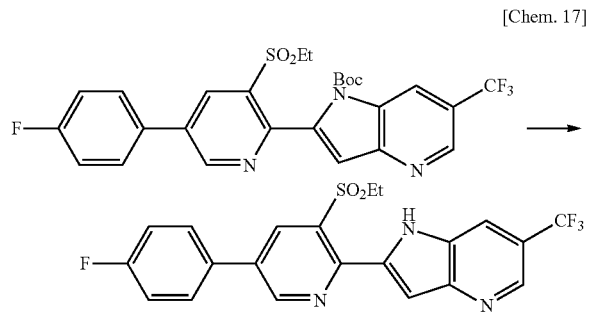

[Chem. 17]

To the 2-(3-ethylsulfonyl-5-(4-fluorophenyl)pyridin-2-yl)-1-tert-butoxycarbonyl-6-trifluoromethyl-1H-pyrrolo[3,2-b]pyridine produced in the previous step, TFA (trifluoroacetic acid) (10 mL) was added, and the mixture was stirred at room temperature overnight. After the completion of the reaction, the reaction mixture was dried in vacuo, and the residue was purified by silica gel chromatography to give the desired compound (0.081 g, 81% (2 steps)).

Example 3

Production Method of 2-(3-Ethylsulfonyl-5-(4-fluorophenyl)pyridin-2-yl)-3,3-difluoro-6-trifluoromethyl-3H-pyrrolo[3,2-b]pyridine (Compound number 1-19)

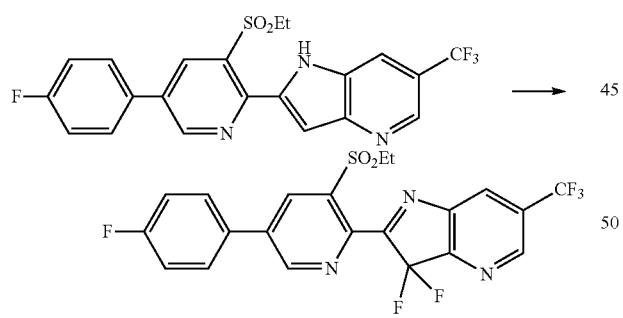

[Chem. 18]

To an acetonitrile solution (3 mL) of the 2-(3-ethylsulfonyl-5-(4-fluorophenyl)pyridin-2-yl)-6-trifluoromethyl-1H-pyrrolo[3,2-b]pyridine (0.06 g) produced in the previous step, $NaHCO_3$ (0.034 g) and Selectfluor (0.14 g) were added at room temperature, and the mixture was stirred at 60° C. for 2 hours. After the completion of the reaction, a saturated aqueous sodium bicarbonate solution and a saturated aqueous sodium thiosulfate solution were added, and ethyl acetate extraction was performed. The organic layer was dried over anhydrous magnesium sulfate and then dried in vacuo, and the residue was purified by silica gel chromatography to give the desired compound (0.044 g, 68%).

Example 4

Production Method of 2-(3-Ethylsulfonyl-5-(3-trifluoromethylphenyl)pyridin-2-yl)-3,3-difluoro-6-trifluoromethyl-3H-pyrrolo[3,2-b]pyridine (Compound number 1-20)

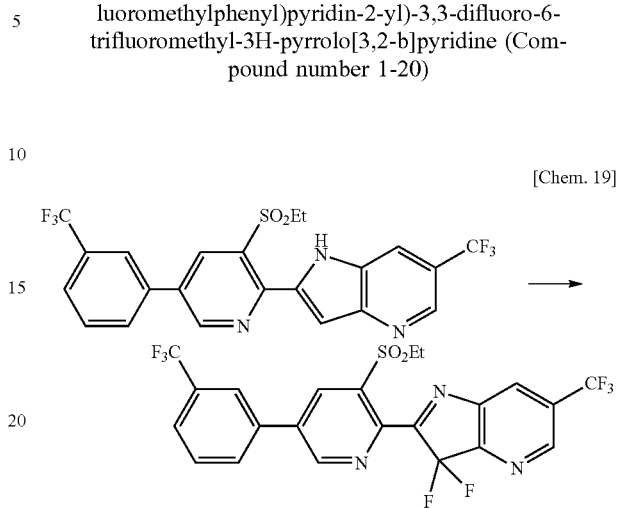

[Chem. 19]

To an acetonitrile solution (3 mL) of 2-(3-ethylsulfonyl-5-(3-trifluoromethylphenyl)pyridin-2-yl)-6-trifluoromethyl-1H-pyrrolo[3,2-b]pyridine (0.06 g), which had been produced by the same method as in the above Reference Example, $NaHCO_3$ (0.034 g) and Selectfluor (0.14 g) were added at room temperature, and the mixture was stirred at 60° C. for 2 hours. After the completion of the reaction, a saturated aqueous sodium bicarbonate solution and a saturated aqueous sodium thiosulfate solution were added, and ethyl acetate extraction was performed. The organic layer was dried over anhydrous magnesium sulfate and then dried in vacuo, and the residue was purified by silica gel chromatography to give the desired compound (0.045 g, 63%).

Hereinafter, formulation examples are shown, but the present invention is not limited thereto. In the formulation examples, the "part" means a part by weight.

Formulation Example 1

| | |
|---|---|
| Compound of the present invention | 10 parts |
| Xylene | 70 parts |
| N-methylpyrrolidone | 10 parts |
| Mixture of polyoxyethylene nonylphenyl ether and calcium alkylbenzene sulfonate | 10 parts |

The above ingredients are uniformly mixed for dissolution to give an emulsifiable concentrate formulation.

Formulation Example 2

| | |
|---|---|
| Compound of the present invention | 3 parts |
| Clay powder | 82 parts |
| Diatomite powder | 15 parts |

The above ingredients are uniformly mixed and then pulverized to give a dust formulation.

Formulation Example 3

| Compound of the present invention | 5 parts |
|---|---|
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granular formulation.

Formulation Example 4

| Compound of the present invention | 20 parts |
|---|---|
| Kaolin and synthetic high-dispersion silicic acid | 75 parts |
| Mixture of polyoxyethylene nonylphenyl ether and calcium alkylbenzene sulfonate | 5 parts |

The above ingredients are uniformly mixed and then pulverized to give a wettable powder formulation.

Hereinafter, test examples in connection with the present invention are shown, but the present invention is not limited thereto.

Test Example 1

Test of Control Effect on *Myzus persicae*

Chinese cabbage plants were planted in plastic pots (diameter: 8 cm, height: 8 cm), green peach aphids (*Myzus persicae*) were propagated on the plants, and the number of surviving green peach aphids in each pot was counted. The condensed heterocyclic compounds represented by the general formula (1) of the present invention or salts thereof were separately dispersed in water and diluted to 500 ppm, and the agrochemical dispersions were applied to the foliage of the potted Chinese cabbage plants. After the plants were air-dried, the pots were kept in a greenhouse. At 6 days after the foliar application, the number of surviving green peach aphids on the Chinese cabbage plant in each pot was counted, the control rate was calculated according to the formula shown below, and the control effect was evaluated according to the criteria shown below.

$$\text{Control rate} = 100 - \{(T \times Ca)/(Ta \times C)\} \times 100 \quad [\text{Math. 1}]$$

Ta: the number of survivors before the foliar application in a treatment plot
T: the number of survivors after the foliar application in a treatment plot
Ca: the number of survivors before the foliar application in a non-treatment plot
C: the number of survivors after the foliar application in a non-treatment plot
Criteria
A: the control rate is 100%.
B: the control rate is 90 to 99%.
C: the control rate is 80 to 89%.
D: the control rate is 50 to 79%.

As a result, the compounds 1-1, 1-2, 1-3, 1-4, 1-5, 1-6, 1-7, 1-9, 1-10, 1-11, 1-12, 1-13, 1-14, 1-15, 1-16, 1-18, 1-19, 1-20, 1-21, 1-34, 1-71, 1-81, 1-99, 1-100, 1-109, 1-169, 1-171, 1-174, 1-176, 1-177, 1-180, 1-181, 1-182, 1-183, 1-184, 1-194, 1-200, 1-202, 1-209, 1-210, 1-211, 1-212, 1-224, 1-226, 1-239, 1-241, 1-257, 1-287, 1-290, 2-1, 2-3, 2-13 and 2-16 of the present invention showed the activity level evaluated as A.

Test Example 2

Insecticidal Test on *Laodelphax striatella*

The condensed heterocyclic compounds represented by the general formula (1) of the present invention or salts thereof were separately dispersed in water and diluted to 500 ppm, and rice plant seedlings (variety: Nihonbare) were dipped in the agrochemical dispersions for 30 seconds. After air-dried, each seedling was put into a separate glass test tube and inoculated with ten 3rd-instar larvae of *Laodelphax striatella*, and then the glass test tubes were capped with cotton plugs. At 8 days after the inoculation, the numbers of surviving larvae and dead larvae were counted, the corrected mortality rate was calculated according to the formula shown below, and the insecticidal effect was evaluated according to the criteria of Test Example 1.

$$\text{Corrected mortality rate (\%)} = 100 \times (\text{Survival rate in a non-treatment plot} - \text{Survival rate in a treatment plot})/\text{Survival rate in a non-treatment plot} \quad [\text{Math. 2}]$$

As a result, the compounds 1-1, 1-2, 1-3, 1-4, 1-5, 1-6, 1-7, 1-9, 1-10, 1-11, 1-12, 1-13, 1-14, 1-15, 1-16, 1-18, 1-19, 1-20, 1-21, 1-34, 1-71, 1-81, 1-99, 1-100, 1-109, 1-169, 1-171, 1-174, 1-176, 1-177, 1-180, 1-181, 1-182, 1-183, 1-184, 1-194, 1-200, 1-202, 1-209, 1-210, 1-211, 1-212, 1-224, 1-226, 1-239, 1-241, 1-257, 1-287, 1-290, 2-1, 2-3, 2-13 and 2-16 of the present invention showed the activity level evaluated as A.

Test Example 3

Insecticidal Test on *Plutella xylostella*

Adults of *Plutella xylostella* were released onto Chinese cabbage seedlings and allowed to lay eggs thereon. At 2 days after the release of the adults, the Chinese cabbage seedlings with laid eggs were dipped for about 30 seconds in agrochemical dispersions diluted to 500 ppm, each of which contained a different condensed heterocyclic compound represented by the general formula (1) of the present invention as an active ingredient. After air-dried, the seedlings were kept in a thermostatic chamber at 25° C. At 6 days after the dip treatment, the number of hatched larvae per plot was counted, the mortality rate was calculated according to the formula shown below, and the insecticidal effect was evaluated according to the criteria of Test Example 1. This test was conducted in triplicate using 10 adults of *Plutella xylostella* per plot.

$$\text{Corrected mortality rate (\%)} = 100 \times (\text{Number of hatched larvae in a non-treatment plot} - \text{Number of hatched larvae in a treatment plot})/\text{Number of hatched larvae in a non-treatment plot} \quad [\text{Math. 3}]$$

As a result, the compounds 1-1, 1-2, 1-3, 1-4, 1-5, 1-6, 1-7, 1-9, 1-10, 1-11, 1-12, 1-13, 1-14, 1-15, 1-16, 1-18, 1-19, 1-20, 1-21, 1-34, 1-71, 1-81, 1-99, 1-100, 1-109, 1-169, 1-171, 1-174, 1-176, 1-177, 1-180, 1-181, 1-182, 1-183, 1-184, 1-194, 1-200, 1-202, 1-209, 1-210, 1-211, 1-212, 1-224, 1-226, 1-239, 1-241, 1-257, 1-287, 1-290, 2-1, 2-3, 2-13 and 2-16 of the present invention showed the activity level evaluated as A.

INDUSTRIAL APPLICABILITY

The compounds of the present invention are highly effective for the control of a wide range of agricultural and horticultural pests and thus are useful.

The invention claimed is:
1. A 3H-pyrrolopyridine compound represented by the general formula (1):

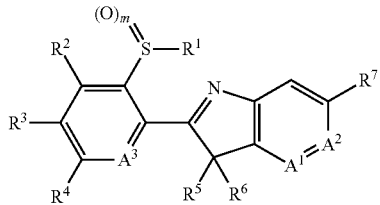

wherein:
R$^1$ represents:
(a1) a ($C_1$-$C_6$) alkyl group;
(a2) a ($C_3$-$C_6$) cycloalkyl group;
(a3) a ($C_2$-$C_6$) alkenyl group; or
(a4) a ($C_2$-$C_6$) alkynyl group,
R$^2$ and R$^4$ may be the same or different and each represent:
(b1) a hydrogen atom;
(b2) a halogen atom;
(b3) a hydroxyl group;
(b4) a formyl group;
(b5) a cyano group;
(b6) a ($C_1$-$C_6$) alkyl group;
(b7) a ($C_3$-$C_6$) cycloalkyl group;
(b8) a ($C_1$-$C_6$) alkoxy group;
(b9) a halo ($C_1$-$C_6$) alkyl group;
(b10) a halo ($C_3$-$C_6$) cycloalkyl group;
(b11) a halo ($C_1$-$C_6$) alkoxy group;
(b12) a ($C_1$-$C_6$) alkylthio group;
(b13) a ($C_1$-$C_6$) alkylsulfinyl group;
(b14) a ($C_1$-$C_6$) alkylsulfonyl group;
(b15) a halo ($C_1$-$C_6$) alkylthio group;
(b16) a halo ($C_1$-$C_6$) alkylsulfinyl group;
(b17) a halo ($C_1$-$C_6$) alkylsulfonyl group;
(b18) a ($C_3$-$C_6$) cycloalkyl ($C_1$-$C_6$) alkoxy group;
(b19) a R$^9$(R$^{10}$)N group (wherein R$^9$ and R$^{10}$ may be the same or different and each represent a hydrogen atom, a ($C_1$-$C_6$) alkyl group, a ($C_3$-$C_6$) cycloalkyl ($C_1$-$C_6$) alkyl group, a halo ($C_1$-$C_6$) alkyl group, a ($C_1$-$C_6$) alkylcarbonyl group, a ($C_1$-$C_6$) alkoxycarbonyl group or a phenylcarbonyl group);
(b20) a mono-($C_1$-$C_6$) alkylaminocarbonyl NH group;
(b21) a mono-($C_1$-$C_6$) alkylaminothiocarbonyl NH group;
(b22) a C(R$^9$)=NOR$^{10}$ group (wherein R$^9$ and R$^{10}$ are as defined above);
(b23) a carboxyl group;
(b24) a ($C_1$-$C_6$) alkoxycarbonyl group;
(b25) a R$^9$(R$^{10}$)N carbonyl group (wherein R$^9$ and R$^{10}$ are as defined above);
(b26) an aryl group;
(b27) an aryl group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(b28) an aryl ($C_1$-$C_6$) alkyl group;

(b29) an aryl ($C_1$-$C_6$) alkyl group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(b30) an aryl ($C_1$-$C_6$) alkyloxy group;
(b31) an aryl ($C_1$-$C_6$) alkyloxy group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(b32) an aryl ($C_1$-$C_6$) alkyl NH group;
(b33) an aryl ($C_1$-$C_6$) alkyl NH group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(b34) a heterocyclic group; or
(b35) a heterocyclic group having, on the ring, 1 to 3 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group,
R$^3$ and R$^7$ may be the same or different and each represent:
(c1) a hydrogen atom;
(c2) a halogen atom;
(c3) a hydroxyl group;
(c4) a formyl group;
(c5) a cyano group;
(c6) a ($C_1$-$C_6$) alkyl group;
(c7) a ($C_3$-$C_6$) cycloalkyl group;
(c8) a ($C_1$-$C_6$) alkoxy group;
(c9) a halo ($C_1$-$C_6$) alkyl group;
(c10) a halo ($C_3$-$C_6$) cycloalkyl group;
(c11) a halo ($C_1$-$C_6$) alkoxy group;
(c12) a ($C_1$-$C_6$) alkylthio group;
(c13) a ($C_1$-$C_6$) alkylsulfinyl group;
(c14) a ($C_1$-$C_6$) alkylsulfonyl group;
(c15) a halo ($C_1$-$C_6$) alkylthio group;
(c16) a halo ($C_1$-$C_6$) alkylsulfinyl group;
(c17) a halo ($C_1$-$C_6$) alkylsulfonyl group;
(c18) a ($C_3$-$C_6$) cycloalkyl ($C_1$-$C_6$) alkoxy group;
(c19) a R$^9$(R$^{10}$)N group (wherein R$^9$ and R$^{10}$ are as defined above);
(c20) a mono-($C_1$-$C_6$) alkylaminocarbonyl NH group;
(c21) a mono-($C_1$-$C_6$) alkylaminothiocarbonyl NH group;
(c22) a C(R$^9$)=NOR$^{10}$ group (wherein R$^9$ and R$^{10}$ are as defined above);
(c23) a carboxyl group;
(c24) a ($C_1$-$C_6$) alkoxycarbonyl group;

(c25) a $R^9(R^{10})N$ carbonyl group (wherein $R^9$ and $R^{10}$ are as defined above);
(c26) an aryl group;
(c27) an aryl group having, on the ring, 1 to 5 substituting groups which may be the same or different and are selected from the group consisting of a halogen atom, a cyano group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(c28) an aryl ($C_1$-$C_6$) alkyl group;
(c29) an aryl ($C_1$-$C_6$) alkyl group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(c30) an aryl ($C_1$-$C_6$) alkyloxy group;
(c31) an aryl ($C_1$-$C_6$) alkyloxy group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(c32) an aryl ($C_1$-$C_6$) alkyl NH group;
(c33) an aryl ($C_1$-$C_6$) alkyl NH group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(c34) a heterocyclic group; or
(c35) a heterocyclic group having, on the ring, 1 to 3 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group, $R^5$ and $R^6$ may be the same or different and each represent:
(d1) a halogen atom;
(d2) a cyano group;
(d3) a ($C_1$-$C_6$) alkyl group;
(d4) a ($C_1$-$C_6$) alkylthio group;
(d5) a ($C_1$-$C_6$) alkylsulfonyl group; or
(d6) a ($C_1$-$C_6$) alkoxycarbonyl group, or alternatively
(d7) $R^5$ and $R^6$ are joined together to form a 3- to 6-membered aliphatic ring, $R^3$ and $R^4$ may be combined to form an aromatic ring, $A^1$, $A^2$ and $A^3$ may be the same or different and each represent a nitrogen atom, N—O or a C—$R^8$ group (wherein $R^8$ represents (e1) a hydrogen atom; or (e2) a halogen atom), and m represents 0, 1 or 2, an N-oxide thereof or a salt thereof.

2. The 3H-pyrrolopyridine compound according to claim 1, an N-oxide thereof or a salt thereof, wherein:
$R^1$ represents (a1) a ($C_1$-$C_6$) alkyl group,
$R^2$ and $R^4$ may be the same or different and each represent:
(b1) a hydrogen atom;
(b2) a halogen atom;
(b3) a hydroxyl group;
(b6) a ($C_1$-$C_6$) alkyl group;
(b7) a ($C_3$-$C_6$) cycloalkyl group;
(b8) a ($C_1$-$C_6$) alkoxy group;
(b9) a halo ($C_1$-$C_6$) alkyl group;
(b11) a halo ($C_1$-$C_6$) alkoxy group;
(b12) a ($C_1$-$C_6$) alkylthio group;
(b14) a ($C_1$-$C_6$) alkylsulfonyl group;
(b15) a halo ($C_1$-$C_6$) alkylthio group;
(b16) a halo ($C_1$-$C_6$) alkylsulfinyl group;
(b18) a ($C_3$-$C_6$) cycloalkyl ($C_1$-$C_6$) alkoxy group;
(b19) a $R^9(R^{10})N$ group (wherein $R^9$ and $R^{10}$ may be the same or different and each represent a hydrogen atom, a ($C_1$-$C_6$) alkyl group, a ($C_3$-$C_6$) cycloalkyl ($C_1$-$C_6$) alkyl group, a halo ($C_1$-$C_6$) alkyl group, a ($C_1$-$C_6$) alkylcarbonyl group, a ($C_1$-$C_6$) alkoxycarbonyl group or a phenylcarbonyl group);
(b20) a mono-($C_1$-$C_6$) alkylaminocarbonyl NH group;
(b21) a mono-($C_1$-$C_6$) alkylaminothiocarbonyl NH group;
(b22) a $C(R^9)=NOR^{10}$ group (wherein $R^9$ and $R^{10}$ are as defined above);
(b23) a carboxyl group;
(b24) a ($C_1$-$C_6$) alkoxycarbonyl group;
(b25) a $R^9(R^{10})N$ carbonyl group (wherein $R^9$ and $R^{10}$ are as defined above);
(b26) an aryl group;
(b27) an aryl group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(b28) an aryl ($C_1$-$C_6$) alkyl group;
(b29) an aryl ($C_1$-$C_6$) alkyl group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(b31) an aryl ($C_1$-$C_6$) alkyloxy group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(b33) an aryl ($C_1$-$C_6$) alkyl NH group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;

(b34) a heterocyclic group; or (b35) a heterocyclic group having, on the ring, 1 to 3 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group, $R^3$ and $R^7$ may be the same or different and each represent:

(c1) a hydrogen atom;
(c2) a halogen atom;
(c6) a ($C_1$-$C_6$) alkyl group;
(c7) a ($C_3$-$C_6$) cycloalkyl group;
(c8) a ($C_1$-$C_6$) alkoxy group;
(c9) a halo ($C_1$-$C_6$) alkyl group;
(c11) a halo ($C_1$-$C_6$) alkoxy group;
(c12) a ($C_1$-$C_6$) alkylthio group;
(c14) a ($C_1$-$C_6$) alkylsulfonyl group;
(c15) a halo ($C_1$-$C_6$) alkylthio group;
(c16) a halo ($C_1$-$C_6$) alkylsulfinyl group;
(c18) a ($C_3$-$C_6$) cycloalkyl ($C_1$-$C_6$) alkoxy group;
(c19) a $R^9(R^{10})N$ group (wherein $R^9$ and $R^{10}$ may be the same or different and each represent a hydrogen atom, a ($C_1$-$C_6$) alkyl group, a ($C_3$-$C_6$) cycloalkyl ($C_1$-$C_6$) alkyl group, a halo ($C_1$-$C_6$) alkyl group, a ($C_1$-$C_6$) alkylcarbonyl group, a ($C_1$-$C_6$) alkoxycarbonyl group or a phenylcarbonyl group);
(c20) a mono-($C_1$-$C_6$) alkylaminocarbonyl NH group;
(c21) a mono-($C_1$-$C_6$) alkylaminothiocarbonyl NH group;
(c22) a $C(R^9)=NOR^{10}$ group (wherein $R^9$ and $R^{10}$ are as defined above);
(c23) a carboxyl group;
(c24) a ($C_1$-$C_6$) alkoxycarbonyl group;
(c25) a $R^9(R^{10})N$ carbonyl group (wherein $R^9$ and $R^{10}$ are as defined above);
(c26) an aryl group;
(c27) an aryl group having, on the ring, 1 to 5 substituting groups which may be the same or different and are selected from the group consisting of a halogen atom, a cyano group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(c28) an aryl ($C_1$-$C_6$) alkyl group;
(c29) an aryl ($C_1$-$C_6$) alkyl group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(c31) an aryl ($C_1$-$C_6$) alkyloxy group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;

(c33) an aryl ($C_1$-$C_6$) alkyl NH group having, on the ring, 1 to 5 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;

(c34) a heterocyclic group; or (c35) a heterocyclic group having, on the ring, 1 to 3 substituting groups which may be the same or different and are selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group, $R^5$ and $R^6$ may be the same or different and each represent:

(d1) a halogen atom;
(d2) a cyano group;
(d3) a ($C_1$-$C_6$) alkyl group;
(d4) a ($C_1$-$C_6$) alkylthio group;
(d5) a ($C_1$-$C_6$) alkylsulfonyl group; or
(d6) a ($C_1$-$C_6$) alkoxycarbonyl group, or alternatively
(d7) $R^5$ and $R^6$ are joined together to form a 3- to 6-membered aliphatic ring, $A^1$, $A^2$ and $A^3$ may be the same or different and each represent a nitrogen atom, N—O or a C—$R^8$ group (wherein $R^8$ represents (e1) a hydrogen atom), and m represents 0, 1 or 2.

3. The 3H-pyrrolopyridine compound according to claim 1, an N-oxide thereof or a salt thereof, wherein:

$R^1$ represents (a1) a ($C_1$-$C_6$) alkyl group, $R^2$ and $R^4$ may be the same or different and each represent (b1) a hydrogen atom; or
(b34) a heterocyclic group, $R^3$ and $R^7$ may be the same or different and each represent:

(c1) a hydrogen atom;
(c2) a halogen atom;
(c7) a ($C_3$-$C_6$) cycloalkyl group;
(c9) a halo ($C_1$-$C_6$) alkyl group;
(c22) a $C(R^9)=NOR^{10}$ group (wherein $R^9$ and $R^{10}$ are as defined above);
(c27) an aryl group having, on the ring, 1 to 5 substituting groups which may be the same or different and are selected from the group consisting of a halogen atom, a cyano group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group and a halo ($C_1$-$C_6$) alkylsulfonyl group;
(c28) an aryl ($C_1$-$C_6$) alkyl group; or
(c34) a heterocyclic group, $R^5$ and $R^6$ may be the same or different and each represent:
(d1) a halogen atom;
(d2) a cyano group;
(d3) a $(C_1-C_6)$ alkyl group; or
(d6) a $(C_1-C_6)$ alkoxycarbonyl group,
$A^1$, $A^2$ and $A^3$ may be the same or different and each represent a nitrogen atom, N—O or a C—$R^8$ group (wherein $R^8$ represents (e1) a hydrogen atom), and
m represents 1 or 2.

4. A method of making an insecticide or ectoparasite control agent comprising:
incorporating the 3H-pyrrolopyridine compound according to claim 1, an N-oxide thereof or a salt thereof into an insecticide or ectoparasite control agent.

5. A method for controlling ectoparasites comprising administering an effective amount of the 3H-pyrrolopyridine compound according to claim 1, an N-oxide thereof or a salt thereof to plants or soil.

6. A method for inhibiting insects or ectoparasites, comprising contacting an insect or ectoparasite with an insecticide or ectoparasite control agent comprising the 3H-pyrrolopyridine compound according to claim 1, an N-oxide thereof or a salt thereof.

7. An ectoparasite control agent or insecticide comprising the 3H-pyrrolopyridine compound according to claim 1, an N-oxide thereof or a salt thereof.

* * * * *

UNITED STATES PATENT AND TRADEMARK OFFICE
CERTIFICATE OF CORRECTION

PATENT NO. : 10,292,395 B2
APPLICATION NO. : 15/775296
DATED : May 21, 2019
INVENTOR(S) : Ikki Yonemura It is certified that error appears in the above-identified patent and that said Letters Patent is hereby corrected as shown below:

In the Specification

In Columns 19-20 at Line 69, Change "represents" to --represent--.

In Columns 21-22 at Line 26, Change "C(Me) =NO" to --C(Me)=NO--.

In Columns 21-22 at Line 27, Change "C(Me) =NO" to --C(Me)=NO--.

In Columns 21-22 at Line 28, Change "C(Me) =NO" to --C(Me)=NO--.

In Columns 21-22 at Line 30, Change "C(CF$_3$) =NO" to --C(CF$_3$)=NO--.

In Columns 21-22 at Line 31, Change "C(CF$_3$) =NO" to --C(CF$_3$)=NO--.

In Columns 23-24 at Line 72, Change "2-CI—Ph" to --2-Cl—Ph--.

In Column 28 at Line 63, Change "Eupoecillia" to --Eupoecilia--.

In Column 29 at Line 22, Change "iwasakii," to --iwasaki,--.

In Column 29 at Line 26, Change "Rhopalosophum" to --Rhopalosiphum--.

In Column 29 at Line 46, Change "Uroeucon" to --Uroleucon--.

In Column 29 at Line 58, Change "Rhopalosophum" to --Rhopalosiphum--.

In Column 29 at Line 66, Change "Macros teles" to --Macrosteles--.

In Column 30 at Line 14, Change "farinose" to --farinosa--.

Signed and Sealed this
Twenty-fifth Day of February, 2020

Andrei Iancu
*Director of the United States Patent and Trademark Office*

CERTIFICATE OF CORRECTION (continued)
U.S. Pat. No. 10,292,395 B2

In Column 30 at Line 57, Change "Hydrellia griseola, Hydrellia griseola," to --Hydrellia griseola,--.

In Column 31 at Line 27, Change "Franklinella" to --Frankliniella--.

In Column 31 at Line 39, Change "sylvairum," to --sylviarum,--.

In Column 31 at Line 43, Change "Octodectes" to --Otodectes--.

In Column 31 at Line 44, Change "ptrenyssnus," to --pteronyssinus,--.

In Column 31 at Line 66, Change "Tylenchus" to --Tylenchulus--.

In Column 32 at Line 3, Change "Lehmannina" to --Lehmannia--.

In Column 32 at Line 17, Change "taiwanesis;" to --taiwanensis;--.

In Column 32 at Line 40, Change "Dalmalinia" to --Damalinia--.

In Column 39 at Line 40, Change "ethofenprox," to --etofenprox,--.

In Column 40 at Line 37, Change "tartarate," to --tartrate,--.

In Column 41 at Line 13, Change "benzensulfonate" to --benzenesulfonate--.

In Column 43 at Line 58, Change "radiobactor," to --radiobacter,--.

In Column 44 at Line 49, After "9H)" insert --.--.